US005723318A

United States Patent [19]
Yamaguchi et al.

[11] Patent Number: 5,723,318
[45] Date of Patent: Mar. 3, 1998

[54] DNA CODING FOR MEGAKARYOCYTE POTENTIATOR

[75] Inventors: Nozomi Yamaguchi, Kyoto; Tetsuo Kojima, Shizuoka; Masayoshi Oh-eda, Shizuoka; Kunihiro Hattori, Shizuoka, all of Japan

[73] Assignee: Chugai Suyaku K.K., Tokyo, Japan

[21] Appl. No.: 426,819

[22] Filed: Apr. 21, 1995

Related U.S. Application Data

[63] Continuation-in-part of PCT/JP93/01540, Oct. 25, 1993.

[30] Foreign Application Priority Data

Oct. 23, 1992 [JP] Japan ................................. 4-286153
Nov. 11, 1992 [JP] Japan ................................. 4-301387
Dec. 9, 1992 [JP] Japan ................................. 4-329546

[51] Int. Cl.$^6$ ........................... C07K 14/52; C12N 15/19
[52] U.S. Cl. .................. 435/69.5; 435/325; 435/252.3; 435/320.1; 435/71.1; 536/23.1; 536/23.5; 536/24.3; 530/351; 530/399
[58] Field of Search ..................... 536/23.1, 23.5, 536/24.3; 435/69.5, 172.3, 260.2, 260.3, 252.3, 320.1, 70.1, 71.1, 71.2, 325; 530/351, 399; 935/4, 11, 22, 52, 70, 66, 72

[56] References Cited

U.S. PATENT DOCUMENTS 5,260,417  11/1993  Grant et al. ............................ 530/351

OTHER PUBLICATIONS

Ishibashi et al., Proc. Natl.Acac. Sci. USA, 86:5953-5957 (1989).
Yonemura et al., Exp. Hematol., 20:1011-1016 (1992).
Metcalf et al., Blood, 77(10):2150-2153 (1991).
Ngo et al. (1994) The Protein Folding Problem & Tertiary Structure Prediction (Merz et al.) Birkhauser Boston 1994.

*Primary Examiner*—John Ulm
*Assistant Examiner*—Prema Mertz
*Attorney, Agent, or Firm*—Birch, Stewart, Kolasch & Birch, LLP

[57] ABSTRACT

Genes coding for a polypeptide having a human megakaryocyte potentiator activity, recombinant vectors containing said genes, host cells that have been transformed with said recombinant vectors, and a process for producing a polypeptide having a human megakaryocyte potentiator activity by first cultivating said transformed host cells and then isolating the desired polypeptide from the culture.

32 Claims, 8 Drawing Sheets

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
        ( A ) LENGTH: 16 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( v ) FRAGMENT TYPE: N-terminal ( v i i ) IMMEDIATE SOURCE:
        ( B ) CLONE: HPCY5

( i x ) FEATURE:
        ( A ) NAME/KEY: Peptide
        ( B ) LOCATION: 1..16
        ( D ) OTHER INFORMATION: /label=peptide
          / note= "amino terminal peptide of Meg POT, = sequence 1 in Table 1"

( x i ) SEQUENCE DESCRIPTION: SEQ ID NO:1:

-continued

```
Leu Ala Gly Glu Xaa Gly Gln Glu Ala Ala Pro Leu Asp Gly Val Leu
1               5                   10                  15
```

( 2 ) INFORMATION FOR SEQ ID NO:2:

( i ) SEQUENCE CHARACTERISTICS:
        ( A ) LENGTH: 16 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( v ) FRAGMENT TYPE: N-terminal ( v i i ) IMMEDIATE SOURCE:
        ( B ) CLONE: HPCY5

( i x ) FEATURE:
        ( A ) NAME/KEY: Peptide
        ( B ) LOCATION: 1..16
        ( D ) OTHER INFORMATION: /label=peptide
            / note= "amino terminal sequence of MegPOT, = sequence 2 in Table 1"

( x i ) SEQUENCE DESCRIPTION: SEQ ID NO:2:

```
Ala Gly Glu Thr Gly Gln Glu Ala Ala Pro Leu Asp Gly Val Leu Ala
1               5                   10                  15
```

( 2 ) INFORMATION FOR SEQ ID NO:3:

( i ) SEQUENCE CHARACTERISTICS:
        ( A ) LENGTH: 16 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( v ) FRAGMENT TYPE: N-terminal ( v i i ) IMMEDIATE SOURCE:
        ( B ) CLONE: HPCY5

( i x ) FEATURE:
        ( A ) NAME/KEY: Peptide
        ( B ) LOCATION: 1..16
        ( D ) OTHER INFORMATION: /label=peptide
            / note= "amino-terminal sequence of MegPOT, = sequence 3 in Table 1"

( x i ) SEQUENCE DESCRIPTION: SEQ ID NO:3:

```
Gly Glu Thr Gly Gln Glu Ala Ala Pro Leu Asp Gly Val Leu Ala Asn
1               5                   10                  15
```

( 2 ) INFORMATION FOR SEQ ID NO:4:

( i ) SEQUENCE CHARACTERISTICS:
        ( A ) LENGTH: 14 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( v ) FRAGMENT TYPE: N-terminal ( v i i ) IMMEDIATE SOURCE:
        ( B ) CLONE: HPCY5

( i x ) FEATURE:
    ( A ) NAME/KEY: Peptide
    ( B ) LOCATION: 1..14
    ( D ) OTHER INFORMATION: /label=peptide
        / note= "consensus sequence from Edman runs of amino
        terminus of MegPOT, derived from sequences of Table 1"

( x i ) SEQUENCE DESCRIPTION: SEQ ID NO:4:

Gly Glu Thr Gly Gln Glu Ala Ala Pro Leu Asp Gly Val Leu
1               5                   10

( 2 ) INFORMATION FOR SEQ ID NO:5:

( i ) SEQUENCE CHARACTERISTICS:
        ( A ) LENGTH: 35 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( v ) FRAGMENT TYPE: internal ( v i i ) IMMEDIATE SOURCE:
        ( B ) CLONE: HPCY5

( i x ) FEATURE:
        ( A ) NAME/KEY: Peptide
        ( B ) LOCATION: 1..35
        ( D ) OTHER INFORMATION: /label=peptide
            / note= "sequence of a Glu-C peptide of MegPOT"

( i x ) FEATURE:
        ( A ) NAME/KEY: Peptide
        ( B ) LOCATION: 6..33
        ( D ) OTHER INFORMATION: /label=peptide
            / note= "region of Glu-C peptide having low frequency
            of usage codons."

( x i ) SEQUENCE DESCRIPTION: SEQ ID NO:5:

Leu Ala Val Ala Leu Ala Gln Lys Asn Val Lys Leu Ser Thr Glu Gln
1               5                   10                  15

Leu Arg Xaa Leu Ala His Arg Leu Ser Glu Pro Pro Glu Asp Leu Asp
            20                  25                  30

Ala Leu Pro
        35

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic primer, T7"

( i i i ) HYPOTHETICAL: NO ( i v ) ANTI-SENSE: NO ( x i ) SEQUENCE DESCRIPTION: SEQ ID NO:6:

TAATACGACT CACTATAGGG                                                        20

( 2 ) INFORMATION FOR SEQ ID NO:7:

( i ) SEQUENCE CHARACTERISTICS:
        ( A ) LENGTH: 21 base pairs (B) TYPE: nucleic acid
                (C) STRANDEDNESS: single
                (D) TOPOLOGY: linear (ii) MOLECULE TYPE: other nucleic acid
                (A) DESCRIPTION: /desc = "synthetic primer, T3-2"

(iv) ANTI-SENSE: NO (xi) SEQUENCE DESCRIPTION: SEQ ID NO:7:

CATGATTACG CCAAGCTCGA A                                                                21

(2) INFORMATION FOR SEQ ID NO:8:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "synthetic primer, N1"

(iii) HYPOTHETICAL: NO (iv) ANTI-SENSE: NO (xi) SEQUENCE DESCRIPTION: SEQ ID NO:8:

GGNGARACNG GNCARGARGC                                                                  20

(2) INFORMATION FOR SEQ ID NO:9:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "synthetic primer, K4S"

(iii) HYPOTHETICAL: NO (iv) ANTI-SENSE: NO (xi) SEQUENCE DESCRIPTION: SEQ ID NO:9:

GCNCARAARA AYGTNAARYT                                                                  20

(2) INFORMATION FOR SEQ ID NO:10:

(i) SEQUENCE CHARACTERISTICS:
                (A) LENGTH: 23 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "synthetic primer, K4-2A"

(iii) HYPOTHETICAL: NO (iv) ANTI-SENSE: YES (ix) FEATURE:
                (A) NAME/KEY: -
                (B) LOCATION: 6..9
                (D) OTHER INFORMATION: /label=alternate
                    / note= "first sequence shown"

(xi) SEQUENCE DESCRIPTION: SEQ ID NO:10:

GCRTCNAGRT CYTCNGGNGG YTC                                                              23

( 2 ) INFORMATION FOR SEQ ID NO:11:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "syntehtic primer, K4-2A"

( i i i ) HYPOTHETICAL: NO ( i v ) ANTI-SENSE: YES ( i x ) FEATURE:
        ( A ) NAME/KEY: -
        ( B ) LOCATION: 6..9
        ( D ) OTHER INFORMATION: /label=alternate
            / note= "second sequence presented"

( x i ) SEQUENCE DESCRIPTION: SEQ ID NO:11:

GCRTCYAART CYTCNGGNGG YTC                                  23

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic primer, 7D1S"

( i i i ) HYPOTHETICAL: NO ( i v ) ANTI-SENSE: NO ( x i ) SEQUENCE DESCRIPTION: SEQ ID NO:12:

CTCTCAACAG AGCAGCTGCG                                      20

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic primer, 7D3S"

( i i i ) HYPOTHETICAL: NO ( i v ) ANTI-SENSE: NO ( x i ) SEQUENCE DESCRIPTION: SEQ ID NO:13:

CTGGCTCACC GGCTCTCTGA                                      20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic primer, 7D1A"

( i i i ) HYPOTHETICAL: NO ( i v ) ANTI-SENSE: YES ( x i ) SEQUENCE DESCRIPTION: SEQ ID NO:14:

AGAGCCGGTG AGCCAGACAG                                                          20

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic primer, 7D2A"

( i i i ) HYPOTHETICAL: NO ( i v ) ANTI-SENSE: YES ( x i ) SEQUENCE DESCRIPTION: SEQ ID NO:15:

GCGCAGCTGC TCTGTTGAGA                                                          20

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic primer, 3AS1"

( i i i ) HYPOTHETICAL: NO ( i v ) ANTI-SENSE: NO ( x i ) SEQUENCE DESCRIPTION: SEQ ID NO:16:

AACTCCTTGG CTTCCCGTGT G                                                        21

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic primer, 7SA1"

( i i i ) HYPOTHETICAL: NO ( i v ) ANTI-SENSE: YES ( x i ) SEQUENCE DESCRIPTION: SEQ ID NO:17:

CGCATCTGGG TTGAGGAATA G                                                        21

( 2 ) INFORMATION FOR SEQ ID NO:18:

( i ) SEQUENCE CHARACTERISTICS:
        ( A ) LENGTH: 33 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( v ) FRAGMENT TYPE: N-terminal ( i x ) FEATURE:
    ( A ) NAME/KEY: Region
    ( B ) LOCATION: 1..16
    ( D ) OTHER INFORMATION: /label=sequence_13a
        / note= "sequence a in Example 13"

( i x ) FEATURE:
    ( A ) NAME/KEY: Region
    ( B ) LOCATION: 4..31
    ( D ) OTHER INFORMATION: /label=sequence_13b
        / note= "sequence (b) in Example 13"

( i x ) FEATURE:
    ( A ) NAME/KEY: Region
    ( B ) LOCATION: 6..33
    ( D ) OTHER INFORMATION: /label=sequence_13c
        / note= "sequence (c) in Example 13"

( i x ) FEATURE:
    ( A ) NAME/KEY: Region
    ( B ) LOCATION: 1..13
    ( D ) OTHER INFORMATION: /label=sequence_25a
        / note= "sequence a in Examples 25 and 28"

( i x ) FEATURE:
    ( A ) NAME/KEY: Region
    ( B ) LOCATION: 4..16
    ( D ) OTHER INFORMATION: /label=sequence_25b
        / note= "sequence (b) in Examples 25 and 28"

( i x ) FEATURE:
    ( A ) NAME/KEY: Region
    ( B ) LOCATION: 6..18
    ( D ) OTHER INFORMATION: /label=sequence_25c
        / note= "sequence (c) in Examples 25 and 28"

( x i ) SEQUENCE DESCRIPTION: SEQ ID NO:18:

```
Ser Arg Thr Leu Ala Gly Glu Thr Gly Gln Glu Ala Ala Pro Leu Asp
1               5                   10                  15
Gly Val Leu Ala Asn Pro Pro Xaa Ile Ser Xaa Leu Xaa Pro Arg Gln
                20                  25                  30
Leu
```

( 2 ) INFORMATION FOR SEQ ID NO:19:

( i ) SEQUENCE CHARACTERISTICS:
        ( A ) LENGTH: 40 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( v ) FRAGMENT TYPE: internal ( v i i ) IMMEDIATE SOURCE:
        ( B ) CLONE: HPCY5

( i x ) FEATURE:
        ( A ) NAME/KEY: Peptide
        ( B ) LOCATION: 1..40
        ( D ) OTHER INFORMATION: /label=fragment
            / note= "sequence of cyanogen bromide fragment of MegPOT
            from cDNA in Table 3"

( i x ) FEATURE:
        ( A ) NAME/KEY: Modified-site
        ( B ) LOCATION: 32
        ( D ) OTHER INFORMATION: /product="is Xaa in COS"

( i x ) FEATURE:
        ( A ) NAME/KEY: Modified-site
        ( B ) LOCATION: 35
        ( D ) OTHER INFORMATION: /product="is Xaa in COS"

( i x ) FEATURE:
    ( A ) NAME/KEY: Modified-site
    ( B ) LOCATION: 37
    ( D ) OTHER INFORMATION: /product="is Xaa in COS"

( i x ) FEATURE:
    ( A ) NAME/KEY: Peptide
    ( B ) LOCATION: 1..16
    ( D ) OTHER INFORMATION: /label=fragment
        / note= "sequence of cyanogen bromide fragment
        representing C-terminus of MegPOT determined in
        Example 28"

( x i ) SEQUENCE DESCRIPTION: SEQ ID NO:19:

```
Asp Ala Leu Arg Gly Leu Leu Pro Val Leu Gly Gln Pro Ile Ile Arg
1               5                   10                  15

Ser Ile Pro Gln Gly Ile Val Ala Ala Trp Arg Gln Arg Ser Ser Arg
            20                  25                  30

Asp Pro Ser Trp Arg Gln Pro Glu
            35                  40
```

( 2 ) INFORMATION FOR SEQ ID NO:20:

( i ) SEQUENCE CHARACTERISTICS:
    ( A ) LENGTH: 9 amino acids
    ( B ) TYPE: amino acid
    ( C ) STRANDEDNESS: Not Relevant
    ( D ) TOPOLOGY: Not Relevant ( i i ) MOLECULE TYPE: peptide ( v ) FRAGMENT TYPE: C-terminal ( i x ) FEATURE:
    ( A ) NAME/KEY: Peptide
    ( B ) LOCATION: 1..9
    ( D ) OTHER INFORMATION: /label=fragment
        / note= "putative sequence of C-terminus of MegPOT
        determined as Asp-N fragment"

( x i ) SEQUENCE DESCRIPTION: SEQ ID NO:20:

```
Asp Pro Ser Trp Arg Gln Pro Glu Arg
1               5
```

( 2 ) INFORMATION FOR SEQ ID NO:21:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic primer, 3S"

( i i i ) HYPOTHETICAL: NO ( i v ) ANTI-SENSE: NO ( x i ) SEQUENCE DESCRIPTION: SEQ ID NO:21:

CTGGCTCACC GGCTCTCTGA                    20

( 2 ) INFORMATION FOR SEQ ID NO:22:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: other nucleic acid (A) DESCRIPTION: /desc = "synthetic primer, G982A"

(iii) HYPOTHETICAL: NO (iv) ANTI-SENSE: YES (xi) SEQUENCE DESCRIPTION: SEQ ID NO:22:

ATGGATCCTT ACCGCCGGAA CCGCGGCCG 29

(2) INFORMATION FOR SEQ ID NO:23:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (ix) FEATURE:
        (A) NAME/KEY: Peptide
        (B) LOCATION: 1..4
        (D) OTHER INFORMATION: /label=processing_site
                / note= "Furin recognition site"

(xi) SEQUENCE DESCRIPTION: SEQ ID NO:23:

Arg Xaa Arg Arg
1

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic primer, T3-2"

(xi) SEQUENCE DESCRIPTION: SEQ ID NO:24:

CATGATTACG CCAAGCTCGA A 21

(2) INFORMATION FOR SEQ ID NO:25:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic primer, 754GA"

(iii) HYPOTHETICAL: NO (xi) SEQUENCE DESCRIPTION: SEQ ID NO:25:

GCTGCCTCCT CCTGGTCCTG GTCCAGGGGT CC 32

(2) INFORMATION FOR SEQ ID NO:26:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "synthetic primer, 754GS"

(xi) SEQUENCE DESCRIPTION: SEQ ID NO:26:

CCAGGACCAG GAGGAGGCAG CCAGGGCGGC                        30

(2) INFORMATION FOR SEQ ID NO:27:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic primer, 850GA"

(xi) SEQUENCE DESCRIPTION: SEQ ID NO:27:

AGCACGGGCA CCAGGCCCCG CAGAGCGTCC                        30

(2) INFORMATION FOR SEQ ID NO:28:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic primer, 850GS"

(xi) SEQUENCE DESCRIPTION: SEQ ID NO:28:

CTGCGGGGCC TGGTGCCCGT GCTGGGCCAG CCC                    33

(2) INFORMATION FOR SEQ ID NO:29:

(i) SEQUENCE CHARACTERISTICS:
        (A) LENGTH: 40 base pairs
        (B) TYPE: nucleic acid
        (C) STRANDEDNESS: Not Relevant
        (D) TOPOLOGY: Not Relevant (ii) MOLECULE TYPE: other nucleic acid (iii) HYPOTHETICAL: NO (ix) FEATURE:
        (A) NAME/KEY: -
        (B) LOCATION: 1..40
        (D) OTHER INFORMATION: /label=fragment
        / note= "amplified product between primers K4S and K4-2A"

(xi) SEQUENCE DESCRIPTION: SEQ ID NO:29:

CTCAACAGAG CAGCTGCGCT GTCTGGCTCA CCGGCTCTCT             40

(2) INFORMATION FOR SEQ ID NO:30:

(i) SEQUENCE CHARACTERISTICS:
        (A) LENGTH: 69 base pairs
        (B) TYPE: nucleic acid
        (C) STRANDEDNESS: Not Relevant
        (D) TOPOLOGY: Not Relevant (ii) MOLECULE TYPE: cDNA (iii) HYPOTHETICAL: NO (xi) SEQUENCE DESCRIPTION: SEQ ID NO:30:

CGCCAACTCC TTGGCTTCCC GTGTGCGGAG GTGTCCGGCC TGAGCACGGA GCGTGTCCGG    60
GAGCTGGCT                                                           69

( 2 ) INFORMATION FOR SEQ ID NO:31:

( i ) SEQUENCE CHARACTERISTICS:
        ( A ) LENGTH: 75 base pairs
        ( B ) TYPE: nucleic acid
        ( C ) STRANDEDNESS: Not Relevant
        ( D ) TOPOLOGY: Not Relevant ( i i ) MOLECULE TYPE: cDNA ( i i i ) HYPOTHETICAL: NO ( x i ) SEQUENCE DESCRIPTION: SEQ ID NO:31:

```
CTCTCTGAGC CCCCCGAGGA CCTGGACGCC CTCCCATTGG ACCTGCTGCT ATTCCTCAAC        60

CCAGATGCGT TCTCG                                                         75
```

( 2 ) INFORMATION FOR SEQ ID NO:32:

( i ) SEQUENCE CHARACTERISTICS:
        ( A ) LENGTH: 197 base pairs
        ( B ) TYPE: nucleic acid
        ( C ) STRANDEDNESS: Not Relevant
        ( D ) TOPOLOGY: Not Relevant ( i i ) MOLECULE TYPE: cDNA ( i x ) FEATURE:
        ( A ) NAME/KEY: -
        ( B ) LOCATION: 1..197
        ( D ) OTHER INFORMATION: /label=fragment
            / note= "amplified product from pool D using primers 3AS1
            and 7SA1"

( i x ) FEATURE:
        ( A ) NAME/KEY: CDS
        ( B ) LOCATION: 3..197

( x i ) SEQUENCE DESCRIPTION: SEQ ID NO:32:

```
AA  CTC CTT GGC TTC CCG TGT GCG GAG GTG TCC GGC CTG AGC ACG GAG           47
    Leu Leu Gly Phe Pro Cys Ala Glu Val Ser Gly Leu Ser Thr Glu
    1               5                   10                  15

CGT GTC CGG GAG CTG GCT GTG GCC TTG GCA CAG AAG AAT GTC AAG CTC          95
Arg Val Arg Glu Leu Ala Val Ala Leu Ala Gln Lys Asn Val Lys Leu
            20                  25                  30

TCA ACA GAG CAG CTG CGC TGT CTG GCT CAC CGG CTC TCT GAG CCC CCC         143
Ser Thr Glu Gln Leu Arg Cys Leu Ala His Arg Leu Ser Glu Pro Pro
        35                  40                  45

GAG GAC CTG GAC GCC CTC CCA TTG GAC CTG CTG CTA TTC CTC AAC CCA         191
Glu Asp Leu Asp Ala Leu Pro Leu Asp Leu Leu Leu Phe Leu Asn Pro
    50                  55                  60

GAT GCG                                                                 197
Asp Ala
65
```

( 2 ) INFORMATION FOR SEQ ID NO:33:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: protein ( x i ) SEQUENCE DESCRIPTION: SEQ ID NO:33:

```
Leu Leu Gly Phe Pro Cys Ala Glu Val Ser Gly Leu Ser Thr Glu Arg
1               5                   10                  15

Val Arg Glu Leu Ala Val Ala Leu Ala Gln Lys Asn Val Lys Leu Ser
            20                  25                  30
```

| | | | | | | | | | | | | | |
|---|---|---|---|---|---|---|---|---|---|---|---|---|---|
|Thr|Glu|Gln|Leu|Arg|Cys|Leu|Ala|His|Arg|Leu|Ser|Glu|Pro|Pro|Glu|
| | |35| | | | |40| | | | |45| | | |

Asp Leu Asp Ala Leu Pro Leu Asp Leu Leu Leu Phe Leu Asn Pro Asp
    50              55                  60

Ala
65

( 2 ) INFORMATION FOR SEQ ID NO:34:

( i ) SEQUENCE CHARACTERISTICS:
        ( A ) LENGTH: 2129 base pairs
        ( B ) TYPE: nucleic acid
        ( C ) STRANDEDNESS: Not Relevant
        ( D ) TOPOLOGY: Not Relevant ( i i ) MOLECULE TYPE: cDNA ( i i i ) HYPOTHETICAL: NO ( v i i ) IMMEDIATE SOURCE:
        ( B ) CLONE: pKP027

( i x ) FEATURE:
        ( A ) NAME/KEY: CDS
        ( B ) LOCATION: 97..1965

( i x ) FEATURE:
        ( A ) NAME/KEY: misc_feature
        ( B ) LOCATION: 1873
        ( D ) OTHER INFORMATION: /note= "this residue is A in
            pKP021"

( x i ) SEQUENCE DESCRIPTION: SEQ ID NO:34:

```
GAATTCGGCA CGAGGCCACT CCCGTCTGCT GTGACGCGCG GACAGAGAGC TACCGGTGGA        60

CCCACGGTGC CTCCCTCCCT GGGATCTACA CAGACC ATG GCC TTG CCA ACG GCT         114
                                        Met Ala Leu Pro Thr Ala
                                                            5

CGA CCC CTG TTG GGG TCC TGT GGG ACC CCC GCC CTC GGC AGC CTC CTG         162
Arg Pro Leu Leu Gly Ser Cys Gly Thr Pro Ala Leu Gly Ser Leu Leu
             10                  15                  20

TTC CTG CTC TTC AGC CTC GGA TGG GTG CAG CCC TCG AGG ACC CTG GCT         210
Phe Leu Leu Phe Ser Leu Gly Trp Val Gln Pro Ser Arg Thr Leu Ala
         25                  30                  35

GGA GAG ACA GGG CAG GAG GCT GCA CCC CTG GAC GGA GTC CTG GCC AAC         258
Gly Glu Thr Gly Gln Glu Ala Ala Pro Leu Asp Gly Val Leu Ala Asn
     40                  45                  50

CCA CCT AAC ATT TCC AGC CTC TCC CCT CGC CAA CTC CTT GGC TTC CCG         306
Pro Pro Asn Ile Ser Ser Leu Ser Pro Arg Gln Leu Leu Gly Phe Pro
55                  60                  65                  70

TGT GCG GAG GTG TCC GGC CTG AGC ACG GAG CGT GTC CGG GAG CTG GCT         354
Cys Ala Glu Val Ser Gly Leu Ser Thr Glu Arg Val Arg Glu Leu Ala
                 75                  80                  85

GTG GCC TTG GCA CAG AAG AAT GTC AAG CTC TCA ACA GAG CAG CTG CGC         402
Val Ala Leu Ala Gln Lys Asn Val Lys Leu Ser Thr Glu Gln Leu Arg
             90                  95                 100

TGT CTG GCT CAC CGG CTC TCT GAG CCC CCG GAG GAC CTG GAC GCC CTC         450
Cys Leu Ala His Arg Leu Ser Glu Pro Pro Glu Asp Leu Asp Ala Leu
            105                 110                 115

CCA TTG GAC CTG CTG CTA TTC CTC AAC CCA GAT GCG TTC TCG GGG CCC         498
Pro Leu Asp Leu Leu Leu Phe Leu Asn Pro Asp Ala Phe Ser Gly Pro
        120                 125                 130

CAG GCC TGC ACC CGT TTC TTC TCC CGC ATC ACG AAG GCC AAT GTG GAC         546
Gln Ala Cys Thr Arg Phe Phe Ser Arg Ile Thr Lys Ala Asn Val Asp
135                 140                 145                 150
```

-continued

| | | | | | | | | | | | | | | | | |
|---|---|---|---|---|---|---|---|---|---|---|---|---|---|---|---|---|
| CTG | CTC | CCG | AGG | GGG | GCT | CCC | GAG | CGA | CAG | CGG | CTG | CTG | CCT | GCG | GCT | 594 |
| Leu | Leu | Pro | Arg | Gly | Ala | Pro | Glu | Arg | Gln | Arg | Leu | Leu | Pro | Ala | Ala | |
| | | | | 155 | | | | 160 | | | | | 165 | | | |
| CTG | GCC | TGC | TGG | GGT | GTG | CGG | GGG | TCT | CTG | CTG | AGC | GAG | GCT | GAT | GTG | 642 |
| Leu | Ala | Cys | Trp | Gly | Val | Arg | Gly | Ser | Leu | Leu | Ser | Glu | Ala | Asp | Val | |
| | | | 170 | | | | | 175 | | | | | 180 | | | |
| CGG | GCT | CTG | GGA | GGC | CTG | GCT | TGC | GAC | CTG | CCT | GGG | CGC | TTT | GTG | GCC | 690 |
| Arg | Ala | Leu | Gly | Gly | Leu | Ala | Cys | Asp | Leu | Pro | Gly | Arg | Phe | Val | Ala | |
| | | 185 | | | | | 190 | | | | | 195 | | | | |
| GAG | TCG | GCC | GAA | GTG | CTG | CTA | CCC | CGG | CTG | GTG | AGC | TGC | CCG | GGA | CCC | 738 |
| Glu | Ser | Ala | Glu | Val | Leu | Leu | Pro | Arg | Leu | Val | Ser | Cys | Pro | Gly | Pro | |
| | 200 | | | | | 205 | | | | | 210 | | | | | |
| CTG | GAC | CAG | GAC | CAG | CAG | GAG | GCA | GCC | AGG | GCG | GCT | CTG | CAG | GGC | GGG | 786 |
| Leu | Asp | Gln | Asp | Gln | Gln | Glu | Ala | Ala | Arg | Ala | Ala | Leu | Gln | Gly | Gly | |
| 215 | | | | 220 | | | | | 225 | | | | | 230 | | |
| GGA | CCC | CCC | TAC | GGC | CCC | CCG | TCG | ACA | TGG | TCT | GTC | TCC | ACG | ATG | GAC | 834 |
| Gly | Pro | Pro | Tyr | Gly | Pro | Pro | Ser | Thr | Trp | Ser | Val | Ser | Thr | Met | Asp | |
| | | | | 235 | | | | 240 | | | | | 245 | | | |
| GCT | CTG | CGG | GGC | CTG | CTG | CCC | GTG | CTG | GGC | CAG | CCC | ATC | ATC | CGC | AGC | 882 |
| Ala | Leu | Arg | Gly | Leu | Leu | Pro | Val | Leu | Gly | Gln | Pro | Ile | Ile | Arg | Ser | |
| | | | 250 | | | | | 255 | | | | | 260 | | | |
| ATC | CCG | CAG | GGC | ATC | GTG | GCC | GCG | TGG | CGG | CAA | CGC | TCC | TCT | CGG | GAC | 930 |
| Ile | Pro | Gln | Gly | Ile | Val | Ala | Ala | Trp | Arg | Gln | Arg | Ser | Ser | Arg | Asp | |
| | | 265 | | | | | 270 | | | | | 275 | | | | |
| CCA | TCC | TGG | CGG | CAG | CCT | GAA | CGG | ACC | ATC | CTC | CGG | CCG | CGG | TTC | CGG | 978 |
| Pro | Ser | Trp | Arg | Gln | Pro | Glu | Arg | Thr | Ile | Leu | Arg | Pro | Arg | Phe | Arg | |
| | 280 | | | | | 285 | | | | | 290 | | | | | |
| CGG | GAA | GTG | GAG | AAG | ACA | GCC | TGT | CCT | TCA | GGC | AAG | AAG | GCC | CGC | GAG | 1026 |
| Arg | Glu | Val | Glu | Lys | Thr | Ala | Cys | Pro | Ser | Gly | Lys | Lys | Ala | Arg | Glu | |
| 295 | | | | 300 | | | | | 305 | | | | | 310 | | |
| ATA | GAC | GAG | AGC | CTC | ATC | TTC | TAC | AAG | AAG | TGG | GAG | CTG | GAA | GCC | TGC | 1074 |
| Ile | Asp | Glu | Ser | Leu | Ile | Phe | Tyr | Lys | Lys | Trp | Glu | Leu | Glu | Ala | Cys | |
| | | | | 315 | | | | 320 | | | | | 325 | | | |
| GTG | GAT | GCG | GCC | CTG | CTG | GCC | ACC | CAG | ATG | GAC | CGC | GTG | AAC | GCC | ATC | 1122 |
| Val | Asp | Ala | Ala | Leu | Leu | Ala | Thr | Gln | Met | Asp | Arg | Val | Asn | Ala | Ile | |
| | | | 330 | | | | | 335 | | | | | 340 | | | |
| CCC | TTC | ACC | TAC | GAG | CAG | CTG | GAC | GTC | CTA | AAG | CAT | AAA | CTG | GAT | GAG | 1170 |
| Pro | Phe | Thr | Tyr | Glu | Gln | Leu | Asp | Val | Leu | Lys | His | Lys | Leu | Asp | Glu | |
| | | 345 | | | | | 350 | | | | | 355 | | | | |
| CTC | TAC | CCA | CAA | GGT | TAC | CCC | GAG | TCT | GTG | ATC | CAG | CAC | CTG | GGC | TAC | 1218 |
| Leu | Tyr | Pro | Gln | Gly | Tyr | Pro | Glu | Ser | Val | Ile | Gln | His | Leu | Gly | Tyr | |
| | 360 | | | | | 365 | | | | | 370 | | | | | |
| CTC | TTC | CTC | AAG | ATG | AGC | CCT | GAG | GAC | ATT | CGC | AAG | TGG | AAT | GTG | ACG | 1266 |
| Leu | Phe | Leu | Lys | Met | Ser | Pro | Glu | Asp | Ile | Arg | Lys | Trp | Asn | Val | Thr | |
| 375 | | | | 380 | | | | | 385 | | | | | 390 | | |
| TCC | CTG | GAG | ACC | CTG | AAG | GCT | TTG | CTT | GAA | GTC | AAC | AAA | GGG | CAC | GAA | 1314 |
| Ser | Leu | Glu | Thr | Leu | Lys | Ala | Leu | Leu | Glu | Val | Asn | Lys | Gly | His | Glu | |
| | | | | 395 | | | | 400 | | | | | 405 | | | |
| ATG | AGT | CCT | CAG | GTG | GCC | ACC | CTG | ATC | GAC | CGC | TTT | GTG | AAG | GGA | AGG | 1362 |
| Met | Ser | Pro | Gln | Val | Ala | Thr | Leu | Ile | Asp | Arg | Phe | Val | Lys | Gly | Arg | |
| | | | 410 | | | | | 415 | | | | | 420 | | | |
| GGC | CAG | CTA | GAC | AAA | GAC | ACC | CTA | GAC | ACC | CTG | ACC | GCC | TTC | TAC | CCT | 1410 |
| Gly | Gln | Leu | Asp | Lys | Asp | Thr | Leu | Asp | Thr | Leu | Thr | Ala | Phe | Tyr | Pro | |
| | | 425 | | | | | 430 | | | | | 435 | | | | |
| GGG | TAC | CTG | TGC | TCC | CTC | AGC | CCC | GAG | GAG | CTG | AGC | TCC | GTG | CCC | CCC | 1458 |
| Gly | Tyr | Leu | Cys | Ser | Leu | Ser | Pro | Glu | Glu | Leu | Ser | Ser | Val | Pro | Pro | |
| | 440 | | | | | 445 | | | | | 450 | | | | | |
| AGC | AGC | ATC | TGG | GCG | GTC | AGG | CCC | CAG | GAC | CTG | GAC | ACG | TGT | GAC | CCA | 1506 |
| Ser | Ser | Ile | Trp | Ala | Val | Arg | Pro | Gln | Asp | Leu | Asp | Thr | Cys | Asp | Pro | |
| 455 | | | | 460 | | | | | 465 | | | | | 470 | | |

| | | | | | | | | | | | | | | | | |
|---|---|---|---|---|---|---|---|---|---|---|---|---|---|---|---|---|
| AGG | CAG | CTG | GAC | GTC | CTC | TAT | CCC | AAG | GCC | CGC | CTT | GCT | TTC | CAG | AAC | 1554 |
| Arg | Gln | Leu | Asp | Val 475 | Leu | Tyr | Pro | Lys | Ala 480 | Arg | Leu | Ala | Phe | Gln 485 | Asn | |
| ATG | AAC | GGG | TCC | GAA | TAC | TTC | GTG | AAG | ATC | CAG | TCC | TTC | CTG | GGT | GGG | 1602 |
| Met | Asn | Gly | Ser 490 | Glu | Tyr | Phe | Val | Lys 495 | Ile | Gln | Ser | Phe | Leu 500 | Gly | Gly | |
| GCC | CCC | ACG | GAG | GAT | TTG | AAG | GCG | CTC | AGT | CAG | CAG | AAT | GTG | AGC | ATG | 1650 |
| Ala | Pro | Thr 505 | Glu | Asp | Leu | Lys | Ala | Leu 510 | Ser | Gln | Gln | Asn | Val 515 | Ser | Met | |
| GAC | TTG | GCC | ACG | TTC | ATG | AAG | CTG | CGG | ACG | GAT | GCG | GTG | CTG | CCG | TTG | 1698 |
| Asp | Leu | Ala 520 | Thr | Phe | Met | Lys 525 | Leu | Arg | Thr | Asp | Ala 530 | Val | Leu | Pro | Leu | |
| ACT | GTG | GCT | GAG | GTG | CAG | AAA | CTT | CTG | GGA | CCC | CAC | GTG | GAG | GGC | CTG | 1746 |
| Thr 535 | Val | Ala | Glu | Val | Gln 540 | Lys | Leu | Leu | Gly | Pro 545 | His | Val | Glu | Gly | Leu 550 | |
| AAG | GCG | GAG | GAG | CGG | CAC | CGC | CCG | GTG | CGG | GAC | TGG | ATC | CTA | CGG | CAG | 1794 |
| Lys | Ala | Glu | Glu | Arg 555 | His | Arg | Pro | Val | Arg 560 | Asp | Trp | Ile | Leu | Arg 565 | Gln | |
| CGG | CAG | GAC | GAC | CTG | GAC | ACG | CTG | GGG | CTG | GGG | CTA | CAG | GGC | GGC | ATC | 1842 |
| Arg | Gln | Asp | Asp 570 | Leu | Asp | Thr | Leu | Gly 575 | Leu | Gly | Leu | Gln | Gly 580 | Gly | Ile | |
| CCC | AAC | GGC | TAC | CTG | GTC | CTA | GAC | CTC | AGC | GTG | CAA | GAG | GCC | CTC | TCG | 1890 |
| Pro | Asn | Gly 585 | Tyr | Leu | Val | Leu | Asp 590 | Leu | Ser | Val | Gln | Glu 595 | Ala | Leu | Ser | |
| GGG | ACG | CCC | TGC | CTC | CTA | GGA | CCT | GGA | CCT | GTT | CTC | ACC | GTC | CTG | GCA | 1938 |
| Gly | Thr | Pro 600 | Cys | Leu | Leu | Gly | Pro 605 | Gly | Pro | Val | Leu | Thr 610 | Val | Leu | Ala | |
| CTG | CTC | CTA | GCC | TCC | ACC | CTG | GCC | TGA | GGGCCCCACT | | CCCTTGCTGG | | | | | 1985 |
| Leu | Leu | Leu 615 | Ala | Ser | Thr | Leu | Ala 620 | * | | | | | | | | |
| CCCCAGCCCT | GCTGGGGATC | CCCGCCTGGC | CAGGAGCAGG | CACGGGTGAT | CCCCGTTCCA | | | | | | | | | | | 2045 |
| CCCCAAGAGA | ACTCGCGCTC | AGTAAACGGG | AACATGCCCC | CTGCAGACAC | GTAAAAAAAA | | | | | | | | | | | 2105 |
| AAAAAAAAAA | AAAAAAACT | CGAG | | | | | | | | | | | | | | 2129 |

( 2 ) INFORMATION FOR SEQ ID NO:35:

( i ) SEQUENCE CHARACTERISTICS:
     ( A ) LENGTH: 622 amino acids
     ( B ) TYPE: amino acid
     ( D ) TOPOLOGY: linear ( i i ) MOLECULE TYPE: protein ( x i ) SEQUENCE DESCRIPTION: SEQ ID NO:35:

| Met 1 | Ala | Leu | Pro | Thr 5 | Ala | Arg | Pro | Leu | Leu 10 | Gly | Ser | Cys | Gly | Thr 15 | Pro |
|---|---|---|---|---|---|---|---|---|---|---|---|---|---|---|---|
| Ala | Leu | Gly | Ser 20 | Leu | Leu | Phe | Leu | Leu 25 | Phe | Ser | Leu | Gly | Trp 30 | Val | Gln |
| Pro | Ser | Arg 35 | Thr | Leu | Ala | Gly | Glu 40 | Thr | Gly | Gln | Glu | Ala 45 | Ala | Pro | Leu |
| Asp | Gly 50 | Val | Leu | Ala | Asn | Pro 55 | Asn | Ile | Ser | Ser | Leu 60 | Ser | Pro | Arg | |
| Gln 65 | Leu | Leu | Gly | Phe | Pro 70 | Cys | Ala | Glu | Val | Ser 75 | Gly | Leu | Ser | Thr | Glu 80 |
| Arg | Val | Arg | Glu | Leu 85 | Ala | Val | Ala | Leu | Ala 90 | Gln | Lys | Asn | Val | Lys 95 | Leu |
| Ser | Thr | Glu | Gln 100 | Leu | Arg | Cys | Leu | Ala 105 | His | Arg | Leu | Ser | Glu 110 | Pro | Pro |
| Glu | Asp | Leu | Asp | Ala | Leu | Pro | Leu | Asp | Leu | Leu | Leu | Phe | Leu | Asn | Pro |

-continued

|     |     |     | 115 |     |     |     | 120 |     |     |     | 125 |     |     |     |
|---|---|---|---|---|---|---|---|---|---|---|---|---|---|---|

Asp Ala Phe Ser Gly Pro Gln Ala Cys Thr Arg Phe Phe Ser Arg Ile
        130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Glu Ala Ala Arg
210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
530                 535                 540

```
Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Val Gln Glu Ala Leu Ser Gly Thr Pro Cys Leu Leu Gly Pro Gly Pro
    595                 600                 605

Val Leu Thr Val Leu Ala Leu Leu Leu Ala Ser Thr Leu Ala
    610                 615                 620
```

( 2 ) INFORMATION FOR SEQ ID NO:36:

( i ) SEQUENCE CHARACTERISTICS:
        ( A ) LENGTH: 584 amino acids
        ( B ) TYPE: amino acid
        ( C ) STRANDEDNESS: Not Relevant
        ( D ) TOPOLOGY: Not Relevant ( i i ) MOLECULE TYPE: protein ( i i i ) HYPOTHETICAL: NO ( v ) FRAGMENT TYPE: internal ( x i ) SEQUENCE DESCRIPTION: SEQ ID NO:36:

```
Gly Glu Thr Gly Gln Glu Ala Ala Pro Leu Asp Gly Val Leu Ala Asn
1               5                   10                  15

Pro Pro Asn Ile Ser Ser Leu Ser Pro Arg Gln Leu Leu Gly Phe Pro
            20                  25                  30

Cys Ala Glu Val Ser Gly Leu Ser Thr Glu Arg Val Arg Glu Leu Ala
        35                  40                  45

Val Ala Leu Ala Gln Lys Asn Val Lys Leu Ser Thr Glu Gln Leu Arg
    50                  55                  60

Cys Leu Ala His Arg Leu Ser Glu Pro Pro Glu Asp Leu Asp Ala Leu
65                  70                  75                  80

Pro Leu Asp Leu Leu Leu Phe Leu Asn Pro Asp Ala Phe Ser Gly Pro
                85                  90                  95

Gln Ala Cys Thr Arg Phe Phe Ser Arg Ile Thr Lys Ala Asn Val Asp
            100                 105                 110

Leu Leu Pro Arg Gly Ala Pro Glu Arg Gln Arg Leu Leu Pro Ala Ala
            115                 120                 125

Leu Ala Cys Trp Gly Val Arg Gly Ser Leu Leu Ser Glu Ala Asp Val
        130                 135                 140

Arg Ala Leu Gly Gly Leu Ala Cys Asp Leu Pro Gly Arg Phe Val Ala
145                 150                 155                 160

Glu Ser Ala Glu Val Leu Leu Pro Arg Leu Val Ser Cys Pro Gly Pro
                165                 170                 175

Leu Asp Gln Asp Gln Gln Glu Ala Ala Arg Ala Ala Leu Gln Gly Gly
            180                 185                 190

Gly Pro Pro Tyr Gly Pro Pro Ser Thr Trp Ser Val Ser Thr Met Asp
        195                 200                 205

Ala Leu Arg Gly Leu Leu Pro Val Leu Gly Gln Pro Ile Ile Arg Ser
    210                 215                 220

Ile Pro Gln Gly Ile Val Ala Ala Trp Arg Gln Arg Ser Ser Arg Asp
225                 230                 235                 240

Pro Ser Trp Arg Gln Pro Glu Arg Thr Ile Leu Arg Pro Arg Phe Arg
                245                 250                 255
```

-continued

| | | | | | | | | | | | | | | |
|---|---|---|---|---|---|---|---|---|---|---|---|---|---|---|
|Arg|Glu|Val|Glu|Lys|Thr|Ala|Cys|Pro|Ser|Gly|Lys|Lys|Ala|Arg|Glu|
| | |260| | | |265| | | |270| | | | | |
|Ile|Asp|Glu|Ser|Leu|Ile|Phe|Tyr|Lys|Lys|Trp|Glu|Leu|Glu|Ala|Cys|
| | |275| | | |280| | | |285| | | | | |
|Val|Asp|Ala|Ala|Leu|Leu|Ala|Thr|Gln|Met|Asp|Arg|Val|Asn|Ala|Ile|
| | |290| | | |295| | | |300| | | | | |
|Pro|Phe|Thr|Tyr|Glu|Gln|Leu|Asp|Val|Leu|Lys|His|Lys|Leu|Asp|Glu|
|305| | | | |310| | | |315| | | | | |320|
|Leu|Tyr|Pro|Gln|Gly|Tyr|Pro|Glu|Ser|Val|Ile|Gln|His|Leu|Gly|Tyr|
| | | | |325| | | |330| | | | |335| |
|Leu|Phe|Leu|Lys|Met|Ser|Pro|Glu|Asp|Ile|Arg|Lys|Trp|Asn|Val|Thr|
| | | |340| | | |345| | | |350| | | | |
|Ser|Leu|Glu|Thr|Leu|Lys|Ala|Leu|Leu|Glu|Val|Asn|Lys|Gly|His|Glu|
| | |355| | | |360| | | |365| | | | | |
|Met|Ser|Pro|Gln|Val|Ala|Thr|Leu|Ile|Asp|Arg|Phe|Val|Lys|Gly|Arg|
| |370| | | |375| | | |380| | | | | | |
|Gly|Gln|Leu|Asp|Lys|Asp|Thr|Leu|Asp|Thr|Leu|Thr|Ala|Phe|Tyr|Pro|
|385| | | |390| | | |395| | | | | | |400|
|Gly|Tyr|Leu|Cys|Ser|Leu|Ser|Pro|Glu|Glu|Leu|Ser|Ser|Val|Pro|Pro|
| | | |405| | | |410| | | | | |415| | |
|Ser|Ser|Ile|Trp|Ala|Val|Arg|Pro|Gln|Asp|Leu|Asp|Thr|Cys|Asp|Pro|
| | |420| | | | |425| | | |430| | | | |
|Arg|Gln|Leu|Asp|Val|Leu|Tyr|Pro|Lys|Ala|Arg|Leu|Ala|Phe|Gln|Asn|
| | |435| | | |440| | | | |445| | | | |
|Met|Asn|Gly|Ser|Glu|Tyr|Phe|Val|Lys|Ile|Gln|Ser|Phe|Leu|Gly|Gly|
| |450| | | |455| | | |460| | | | | | |
|Ala|Pro|Thr|Glu|Asp|Leu|Lys|Ala|Leu|Ser|Gln|Gln|Asn|Val|Ser|Met|
|465| | | |470| | | |475| | | | | |480| |
|Asp|Leu|Ala|Thr|Phe|Met|Lys|Leu|Arg|Thr|Asp|Ala|Val|Leu|Pro|Leu|
| | | |485| | | |490| | | | |495| | | |
|Thr|Val|Ala|Glu|Val|Gln|Lys|Leu|Leu|Gly|Pro|His|Val|Glu|Gly|Leu|
| | |500| | | |505| | | |510| | | | | |
|Lys|Ala|Glu|Glu|Arg|His|Arg|Pro|Val|Arg|Asp|Trp|Ile|Leu|Arg|Gln|
| |515| | | |520| | | |525| | | | | | |
|Arg|Gln|Asp|Asp|Leu|Asp|Thr|Leu|Gly|Leu|Gly|Leu|Gln|Gly|Gly|Ile|
|530| | | |535| | | |540| | | | | | | |
|Pro|Asn|Gly|Tyr|Leu|Val|Leu|Asp|Leu|Ser|Val|Gln|Glu|Ala|Leu|Ser|
|545| | | |550| | | |555| | | | | | |560|
|Gly|Thr|Pro|Cys|Leu|Leu|Gly|Pro|Gly|Pro|Val|Leu|Thr|Val|Leu|Ala|
| | | |565| | | |570| | | | |575| | | |
|Leu|Leu|Leu|Ala|Ser|Thr|Leu|Ala| | | | | | | | |
| | | |580| | | | | | | | | | | | |

( 2 ) INFORMATION FOR SEQ ID NO:37:

( i ) SEQUENCE CHARACTERISTICS:
        ( A ) LENGTH: 248 amino acids
        ( B ) TYPE: amino acid
        ( C ) STRANDEDNESS: Not Relevant
        ( D ) TOPOLOGY: Not Relevant ( i i ) MOLECULE TYPE: protein ( i i i ) HYPOTHETICAL: NO ( v ) FRAGMENT TYPE: internal ( x i ) SEQUENCE DESCRIPTION: SEQ ID NO:37:

-continued

| | | | | | | | | | | | | | | |
|---|---|---|---|---|---|---|---|---|---|---|---|---|---|---|
| Gly 1 | Glu | Thr | Gly | Gln 5 | Glu | Ala | Ala | Pro | Leu 10 | Asp | Gly | Val | Leu | Ala Asn 15 |
| Pro | Pro | Asn | Ile 20 | Ser | Ser | Leu | Ser | Pro 25 | Arg | Gln | Leu | Leu | Gly 30 | Phe Pro |
| Cys | Ala | Glu 35 | Val | Ser | Gly | Leu | Ser 40 | Thr | Glu | Arg | Val | Arg 45 | Glu | Leu Ala |
| Val | Ala 50 | Leu | Ala | Gln | Lys | Asn 55 | Val | Lys | Leu | Ser | Thr 60 | Glu | Gln | Leu Arg |
| Cys 65 | Leu | Ala | His | Arg 70 | Leu | Ser | Glu | Pro | Pro | Glu 75 | Asp | Leu | Asp | Ala Leu 80 |
| Pro | Leu | Asp | Leu | Leu 85 | Leu | Phe | Leu | Asn | Pro 90 | Asp | Ala | Phe | Ser | Gly Pro 95 |
| Gln | Ala | Cys | Thr 100 | Arg | Phe | Phe | Ser | Arg 105 | Ile | Thr | Lys | Ala | Asn 110 | Val Asp |
| Leu | Leu | Pro 115 | Arg | Gly | Ala | Pro | Glu 120 | Arg | Gln | Arg | Leu | Leu 125 | Pro | Ala Ala |
| Leu | Ala 130 | Cys | Trp | Gly | Val | Arg 135 | Gly | Ser | Leu | Leu | Ser 140 | Glu | Ala | Asp Val |
| Arg 145 | Ala | Leu | Gly | Gly | Leu 150 | Ala | Cys | Asp | Leu | Pro 155 | Gly | Arg | Phe | Val Ala 160 |
| Glu | Ser | Ala | Glu | Val 165 | Leu | Leu | Pro | Arg | Leu 170 | Val | Ser | Cys | Pro | Gly Pro 175 |
| Leu | Asp | Gln | Asp 180 | Gln | Gln | Glu | Ala | Ala 185 | Arg | Ala | Ala | Leu | Gln 190 | Gly Gly |
| Gly | Pro | Pro 195 | Tyr | Gly | Pro | Pro | Ser 200 | Thr | Trp | Ser | Val | Ser 205 | Thr | Met Asp |
| Ala | Leu 210 | Arg | Gly | Leu | Leu | Pro 215 | Val | Leu | Gly | Gln | Pro 220 | Ile | Ile | Arg Ser |
| Ile 225 | Pro | Gln | Gly | Ile | Val 230 | Ala | Ala | Trp | Arg | Gln 235 | Arg | Ser | Ser | Arg Asp 240 |
| Pro | Ser | Trp | Arg | Gln 245 | Pro | Glu | Arg | | | | | | | |

DNA CODING FOR MEGAKARYOCYTE POTENTIATOR

This application is a continuation-in-part of PCT international application No. PCT/JP93/01540 which has an international filing date of Oct. 25, 1993 which designated the United States, the entire contents of which are hereby incorporated by reference.

TECHNICAL FIELD

This invention relates to genes, more particularly, to genes that code for polypeptides having the activity of a megakaryocyte potentiator (hereinafter also abbreviated as Meg-POT) of human origin that acts on megakaryocyte colony-forming units differentiating from pluripotent blood stem cells and which promotes the maturation of megakaryocytes in the presence of a substance such as interleukin 3 (IL-3) that has the activity of a megakaryocyte colony-stimulating factor (hereinafter abbreviated as Meg-CSF). The invention also relates to recombinant vectors containing said genes, cells that have been transformed by those vectors, and a process for producing a megakaryocyte potentiator using said genes.

The genes of the present invention code for a megakaryocyte potentiator which is capable of in vitro amplification of megakaryocyte colonies in a dose-dependent manner in the presence of IL-3. After inserting the genes of the present invention into a suitable vector, conventional host cells are transformed with the vector to produce homogeneous megakaryocyte potentiators in a large volume. Thus, the present invention enables a medicament to be provided that holds promise for finding clinical utility in diseases, typically those which are accompanied by a lower platelet count or malfunction of platelets.

BACKGROUND ART

Platelets are one of the corporeal components of the blood having important significance with respect to hemostasis and thrombus formation in the body. Platelets are released into the blood from mature megakaryocytes formed from hematopoietic stem cells in bone marrow via megakaryocytic precursor cells and megakaryoblasts.

Factors having two different types of action are considered to be required to form megakaryocyte colonies from myeloid cells (Williams, N. et al., "J. Cell Physiol.", 110, 101, 1982). More specifically, these factors consist of Meg-CSF, which by itself results in the formation of megakaryocyte colonies, and Meg-POT, which, although does not result in the formation of megakaryocyte colonies by itself, increases the number of megakaryocyte colonies and promotes their maturation when added together with Meg-CSF.

In human, IL-3 (Teramura, M. et al., "Exp. Hematol.", 16,843, 1988) and granulocyte-macrophage colony stimulating factor (Teramura, M. et al., "Exp. Hematol.", 17, 1011, 1989) are known to be substances having Meg-CSF activity. In addition, examples of substances having Meg-POT activity in human include interleukin 6 (Teramura, M. and Mizoguchi, H., "Int. J. Cell Cloning", 8 245, 1990), interleukin 11 (Teramura, M. et al., "Blood", 79, 327, 1992), and erythropoietin (Bruno, E. et al., "Blood", 73,671, 1989).

However, it is also known that these substances are not specific factors for the megakaryocyte-platelet system, but rather also act on other blood cells as well as on cells outside the blood cell system. Thus, in the case of administration of these substances as pharmaceuticals in anticipation of their action on the megakaryocyte and platelet systems, there is also the risk of the manifestation of other actions different from that which is expected. As such, there is a need for a physiologically active substance having a high degree of usefulness as a pharmaceutical product that specifically acts on the megakaryocyte-platelet system.

A need has, therefore, existed not only for finding a novel megakaryocyte potentiator that acts on the megakaryocyte-platelet system but also for producing that megakaryocyte potentiator in a sufficiently high volume to enable its medical use. A method is known that isolates the megakaryocyte potentiator from the supernatant of a culture of cells capable of producing said potentiator; however, the concentration of megakaryocyte potentiators in the supernatant of the culture is so low that in order to obtain homogeneous megakaryocyte potentiators, a complex sequence of purifying steps are necessary and yet the desired potentiators can only be recovered in small quantities. Hence, it has long been desired that a novel megakaryocyte potentiator which acts on the megakaryocyte-platelet system be produced in large quantities by the recombinant DNA technology so that it can be used for medical purposes.

Under the circumstances, the present inventors found a megakaryocyte potentiating activity in the supernatant of a culture of cloned cells "HPC-Y5" derived from human pancreatic cancer cells, purified the desired novel megakaryocyte potentiator using the megakaryocyte potentiating activity as a marker, and identified the characteristics of that potentiator [International Application No. PCT/JP92/01689 (International Publication No. W093/13132)].

Further, the present inventors synthesized an oligonucleotide primer on the basis of the information about the amino acid sequence of the potentiator. In a separate step, the inventors constructed a cDNA library from the mRNA prepared from "HPC-Y5". Using the synthesized primer, the inventors carried out a polymerase chain reaction (hereunder abbreviated as PCR) to form DNA fragments coding for the megakaryocyte potentiator. In the next step, using these DNA fragments as probes, the inventors screened the cDNA library for successfully isolating genes that would encode the desired novel megakaryocyte potentiator. The inventors even succeeded in identifying the entire base sequence of the isolated genes.

The inventors then inserted the genes into suitable vectors, transformed host cells using the resulting expression vectors and cultivated the transformants. As it turned out, a novel megakaryocyte potentiator could be prepared on a large scale by separating and purifying the expressed protein.

SUMMARY OF THE INVENTION

An object, therefore, of the present invention is to provide genes coding for a polypeptide that has a human megakaryocyte potentiator activity.

Another object of the present invention is to provide a recombinant vector that contains genes coding for a polypeptide that has a human megakaryocyte potentiator activity.

A further object of the present invention is to provide prokaryotic or eukaryotic host cells that have been transformed with a recombinant vector that contains genes coding for a polypeptide that has a human megakaryocyte potentiator activity.

Still another object of the present invention is to provide a process for producing a protein having a human megakaryocyte potentiator activity, which process comprises transforming cells with a recombinant vector that contains genes coding for a polypeptide that has a human megakaryocyte potentiator activity, cultivating the transformants, and separating the produced end protein.

DETAILED DESCRIPTION OF THE INVENTION

Figure 1:
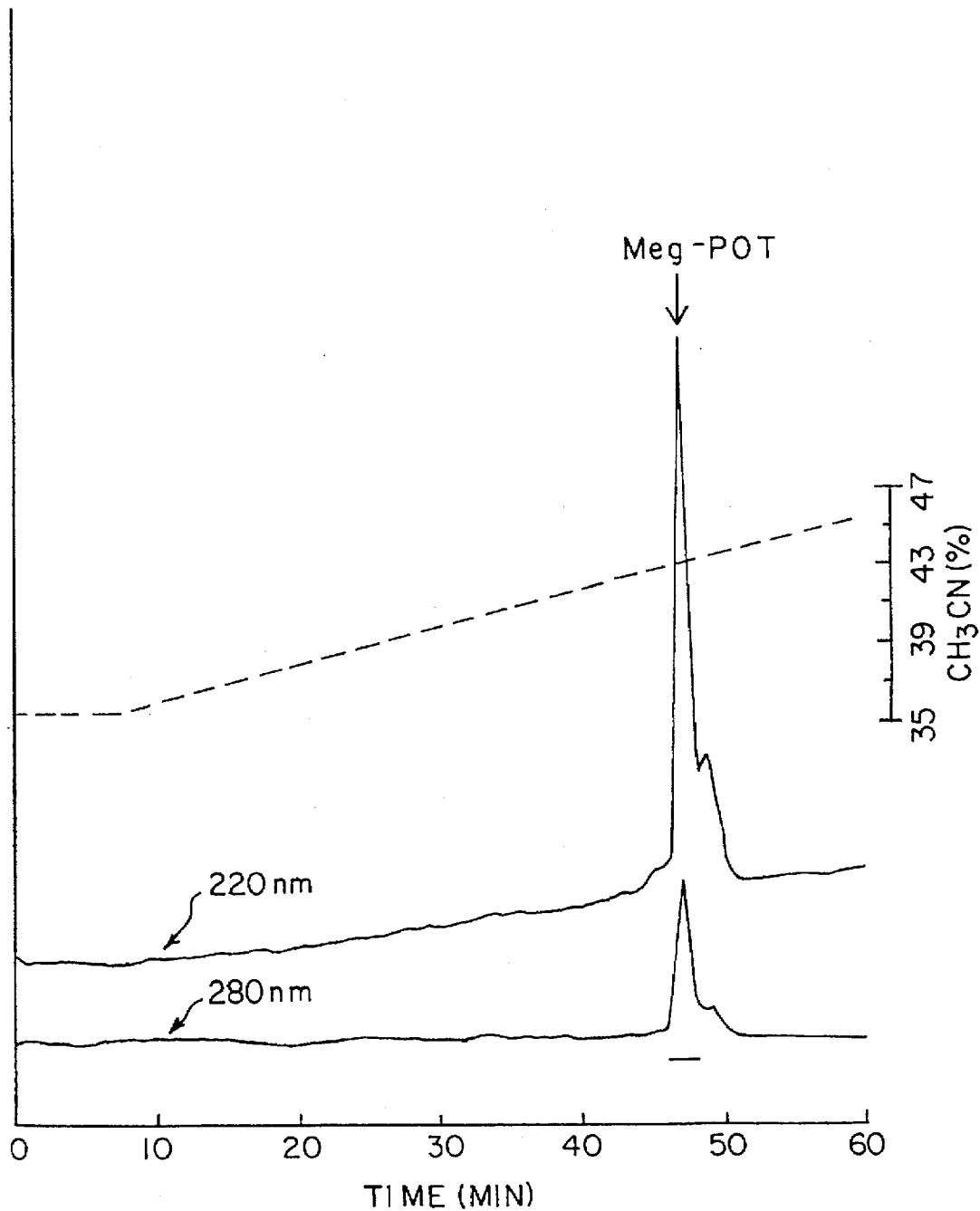
FIG. 1 shows the result of reverse-phase HPLC (III) that was performed in step 7 of the process practiced in Example 3.

The genes of a megakaryocyte potentiator may typically be obtained by first preparing mRNA from cells or the like that produce the megakaryocyte potentiator and then converting it to a double-stranded cDNA by a known technique. The cell line used in the present invention as a source of supply of mRNA was cloned cell line "HPC-Y5" derived from human pancreatic cancer cells (Nozomi Yamaguchi et al., CANCER RESEARCH, 50, 7008, 1990) that were deposited internationally as FERM BP-3703 under the terms of the Budapest Treaty with the Fermentation Research Institute, Agency of Industrial Science and Technology on Dec. 27, 1991. It should, however, be noted that cancer cell lines are not the sole source of supply of mRNA and cells separable from mammalian animals, as well as other established cell lines can also be used.

To prepare mRNA in the present invention, treatment with guanidine thiocyanate was followed by cesium chloride density gradient centrifugation (Chirgwin et al., Biochemistry, 18, 5294, 1979) to yield the total RNA. If desired, methods that have already been employed to clone the genes of other physiologically active proteins may be used, as exemplified by treatments with a surfactant and phenol in the presence of a ribonuclease inhibitor such as a vanadium complex (Berger & Birkenmeier, Biochemistry, 18, 5143, 1979).

Preparation of poly(A)$^+$ RNA from the total RNA can be effected by either affinity column chromatography or a batch method that uses an oligo(dT) bound carrier such as Sepharose or cellulose. The prepared poly(A)$^+$ RNA may be further purified by sucrose density gradient centrifugation or the like. Another method that can be adopted is to obtain poly(A)$^+$ RNA directly without preparing RNA in the first step.

The thus prepared mRNA may be converted to a double-stranded cDNA by the following procedure: with the mRNA used as a template, a reverse transcriptase treatment is effected using either an oligo(dT) complementary to the poly A chain at the 3' end or a random primer or a synthetic oligonucleotide primer that corresponds to a partial amino acid sequence of the megakaryocyte potentiator, whereby cDNA, a DNA complementary to the mRNA, is synthesized.

After degrading and removing the mRNA by alkali treatment, the resulting single-stranded cDNA as it is used as a template is treated with reverse transcriptase or DNA polymerase (e.g. Klenow fragment), followed by treatment with nuclease S1 to yield a double-stranded cDNA. Alternatively, direct treatment with RNase H and DNA polymerase or The like can yield the double-stranded cDNA (Maniatis et al., Molecular Cloning, Cold Spring Harbor Laboratory, 1982 and Gubler & Hoffman, Gene, 25, 263, 1983).

Isolation of cDNA coding for the megakaryocyte potentiator may be performed by various methods such as the use of the megakaryocyte potentiating activity as a marker or carrying out direct expression cloning using an antibody.

The megakaryocyte potentiating activity can be measured by soft agar culturing using myeloid cells in the presence of IL-3.

In the first step, 0.2 ml of equine serum (heated for 30 minutes at 56° C., Biocell), 0.1 ml of mouse (C57BL/6N males, 6–12 weeks old) femur myeloid cells ($2 \times 10^5$ nucleated cells), 0.2 ml of Iscove's Modified Dulbeceo's medium (IMDM) containing 5 ng/ml of recombinant mouse IL-3, 0.4 ml of modified McCoy's 5A medium containing 0.75% agar, and 0.1 ml of the test sample (diluted with IMDM containing 10% equine serum) are mixed and placed in a tissue culture plastic dish having a diameter of 35 mm. After allowing the mixture to solidity, the culture is grown at 37° C. and 100% humidity, in the presence of 5% carbon dioxide gas and 95% air.

On the 6th day of culturing, each agar layer is removed, placed on a glass slide and allowed to dry. The film-like specimens are then fixed with 5% glutaraldehyde, followed by acetylcholinesterase staining and determination of the number of megakaryocyte colonies, according to the method of Nakeff ("Proc. Soc. Exp. Biol. Med.", 151, 587, 1976). At this time, clumps of cells containing 4 or more acetylcholinesterase positive cells are considered to be megakaryocyte colonies. The magnification of the microscope is 40×. The difference between the number of megakaryocyte colonies formed where the test sample was added, and the number of megakaryocyte colonies formed where recombinant IL-3 alone was added without adding the test sample (adding only IMDM containing 10% equine serum as solvent), is taken to be a measure of Meg-POT activity.

The present inventors isolated and purified a megakaryocyte potentiator from the supernatant of a culture of cloned cells capable of producing the megakaryocyte potentiator. The inventors then synthesized a primer based on the information of the amino acid sequence of the potentiator and performed PCR to clone gene fragments that would code for a polypeptide having a human megakaryocyte potentiating activity. Using those DNA fragments as probes, the inventors screened a cDNA library using a known method in order to isolate clones that contained full-length cDNAs coding for the desired novel megakaryocyte potentiator.

E. coli strain JM 109 containing RKPO27 which had these cDNAs inserted between the EcoRI and XhoI cleavage site of pBlue script SK(−), and E. coli strain JM 109 containing pKPO21 were already deposited internationally with the Fermentation Research Institute, Agency of Industrial Science and Technology, under the terms of the Budapest Treaty, as FERM BP-4029 on Oct. 12, 1992, and as FERM BP-4071 on Nov. 10, 1992, respectively.

If desired, full-length cDNAs can be produced by repeating the the PCR carried out in the present invention, instead of the PCR, the probes synthesized on the basis of The information on the known amino acid sequence may be used for direct screening of a cDNA library in order to obtain the desired cDNA.

The thus cloned genes coding for the megakaryocyte potentiator are then incorporated into suitable vector DNAs for transforming other prokaryotic or eukaryotic host cells.

Furthermore, suitable promoters or expression-related sequences may be introduced into the vectors to accomplish gene expression in the respective host cells. If desired, genes coding for other polypeptides may be linked to the desired genes to express them as a fusion protein that can be purified easily or expressed in an increased volume; alternatively, the expressed protein may be subjected to a suitable treatment in the step of purification so that the desired protein can be cleaved. One may also attempt to link genes of another physiologically active factor and enhance the megakaryocyte potentiating activity as it exists in the fusion protein.

As is typically known in the case of human interferon genes, The genes of eukaryotic organisms are generally held to exhibit polymorphism (e.g., Nishi et al., J. Biochem., 97, 153, 1985); this phenomenon may cause replacement of one or more amino acids or, in some cases, the base sequence may change but there is no chance at all in amino acids.

The megakaryocyte potentiating activity may also occur in a polypeptide that is deficient in or added with one or more amino acids in the amino acid sequence tagged with the sequence identification number 36 or 37, or a polypeptide that has one or its amino acids replaced by one or more amino acids. For example, it is already known that a polypeptide that is prepared by converting the base sequence coding for cysteine of a human interleukin 2 (IL-2) gene to the sequence coding for serine, retains IL-2 activity (Wang et al., Science, 224, 1431, 1984).

In most cases of expression in eukaryotic cells, the addition of sugar chains is manifested and this can be adjusted by conversion of one or more amino acids; the polypeptide prepared in this manner may occasionally have the megakaryocyte potentiating activity. Therefore, all genes that code for the polypeptides which are prepared using artificial modifications of the genes of the megakaryocyte potentiator of the present invention shall be included within the scope of the present invention. If necessary, one may prepare genes that code for polypeptides in which amino acids are converted randomly; alternatively, one may prepare genes coding for various modified polypeptides by replacing or deleting base sequences with reference being made to the amino acid sequences of proteins that have the megakaryocyte potentiating activity inherent in non-human animal species (e.g., mouse, rat, monkey, etc.).

It should also be noted that those genes which hybridize with the genes designated by the sequence identification number 36 or 37 and which code for polypeptides that have the megakaryocyte potentiating activity are also included within the scope of the present invention. Hybridization may be performed under those conditions which are adopted for conventional probe hybridization (e.g., Sambrook et al., Molecular Cloning: A Laboratory Manual, Cold Spring Harbor Laboratory Press, 1989).

The expression vectors that can be used in the present invention include a replication origin, selection markers, a promoter situated upstream of the gene to be expressed, RNA splice sites and polyadenylation signals.

For gene expression in mammalian animal cells, various promoters may be used, including promoters derived from viruses such as retrovirus, polyoma virus, adenovirus, simian virus 40 (SV 40) and cellular promoters such as human polypeptide chain elongation factor 1α (HEF-1α). If SV 40 promoter is to be used, gene expression can be easily implemented in accordance with the method of Mulligan et al. (Nature, 277, 108, 1979).

Exemplary replication origins that can be used in the present invention include those which are derived from SV 40, polyoma virus, adenovirus and bovine papilloma virus (BPV). Exemplary selection markers that can be used in the present invention include the phosphotransferase APH (3') II or I (neo) gene, thymidine kinase (TK) gene, E. coli xanthine-guaninephosphoribosyl transferase (Ecogpt) gene, and dihydrofolate reductase (DHFR) gene.

In the case of prokaryotic host cells, for example, E. coli, transformation can be effected using pBR322 which is a plasmid vector which utilizes E. coli as a host (Boliver et al., Gene, 2, 95, 1975). The plasmid pBR322 contains both ampicillin- and tetracycline-resistance genes and transformed cells can be identified on the bases of resistance to either drug. Examples of a promoter that is necessary for gene expression in prokaryotic host organisms include the β-lactamase gene promoter (Chang et al., Nature, 275, 615, 1978), lactose promoter (Goeddel et al., Nature, 281, 544, 1979), tryptophan promoter (Goeddel et al., Nucleic Acid Res., 8, 4057, 1980) and tac promoter, Any of these promoters can be used in expressing the human megakaryocyte potentiator of the present invention.

Exemplary prokaryotic cells that can be used as hosts for the expression system in the present invention include Escherichia coli, Bacillus subtilis and Bacillus thermophilus. Eukaryotic cells can also be used as hosts and exemplary eukaryotic microorganisms include Saccharomyces cerevisiae, and exemplary host cells derived from mammalian animals include COS, Chinese Hamster Ovary (CHO), C127, 3T3, Hela, BHK and Namalwa cells. In the present invention, transformants may be cultivated under appropriate conditions selected for the specific host cells to be used.

The thus cultivated transformants, or host cells that have been transformed with genes coding for the megakaryocyte potentiator, will produce the megakaryocyte potentiator which can be separated either intracellularly or extracellularly and purified to homogeneity.

It should be noted here that the human megakaryocyte potentiator which is the protein of the present invention may be separated and purified by any procedures that are used to separate and purify ordinary proteins. For example, suitable techniques that are selected from among various chromatographic procedures, ultrafiltration, salting-out, dialysis, etc. may be combined appropriately to separate and purify the human megakaryocyte potentiator.

The following examples are provided for the purpose of further illustrating the method of providing genes coding for the megakaryocyte potentiator of the present invention, recombinant vectors having those genes, transformants containing those vectors, the end proteins fielded by culturing the transformants, as well as the processes for producing those recombinant vectors, transformants and proteins. It should, however, be noted that the present invention is in no way limited by these examples.

EXAMPLE 1

Establishment of Meg-POT Producing Cells Line, HPC-Y5

A tumor obtained from the lymph node of a pancreatic cancer patient was cultured in a carbon dioxide gas incubator (carbon dioxide gas concentration 5%, humidity 100%) using RPMI1640 medium containing 10% fetal bovine. serum (FBS) in order to establish a stable cell line. The cloned cells were first acclimated in Ham's F10 medium containing 1% FBS. and further acclimated by gradually decreasing the FBS concentration until ultimately the cells were able to grow in Ham's F10 medium not containing any protein. The present cloned cells grew to form a single layer in a plastic dish, and doubling approximately every 33 hours (see Nozomi Yamaguchi et el., CANCER RESEARCH, 50, 7008, 1990). The cloned cells were designated "HPC-Y5 cells".

EXAMPLE 2

Subculturing of HPC-Y5 and Large Scale Culturing in Roller Bottles

The HPC-Y5 cells described in Example 1 were subcultured in the manner indicated below. The HPC-Y5 cells were cultured in 50 ml of Ham's nutrient Mixture F12 medium containing $10^{-6}$M sodium selenite, 100 U/ml of penicillin G potassium and 100 µg/ml of kanamycin sulfate, using a plastic culturing flask (150 cm$^2$, Corning). The culture medium was replaced every 4 days.

For subculturing, the culture medium was removed and Dulbecco's PBS solution not containing Ca or Mg, but containing 0.125% trypsin (Gibco) and 0.01% EDTA (Wako Pure Chemical Industries) warmed in advance to 37° C., was added, followed by warming for 5 minutes at 37° C. The cells were detached from the culturing flask by pipetting and transferred to a plastic centrifuge tube having a volume of 15 ml. The cells were then collected by centrifuging at a speed of 1500 revolutions/minute for 5 minutes. The cells were then suspended in the above-mentioned medium and distributed into 4–5 new flasks. After allowing to stand overnight, the culture medium along with those cells not adhered to the flasks was removed, followed by the addition of the above-mentioned medium and continuation of culturing. The culture medium was replaced every 4 days thereafter.

In addition, large scale culturing of HPC-Y5 cells using roller bottles for use in purification of the Meg-POT to be described in Example 3 was performed as described below.

HPC-Y5 cells subcultured in the manner described above were collected using trypsin and EDTA in the manner above from the 150 cm$^2$ plastic culture flasks in which the HPC-Y5 cells had confluently grown. The cells were then suspended in 250 ml of the above-mentioned medium containing 0.2% fetal bovine serum (Hyclone), transferred into a 1700 cm$^2$ plastic roller bottle (Corning), and roll cultured at a rate of 0.5 revolutions/minute. After 7 days, the culture medium was replaced by the above-mentioned medium not containing serum, and the above-mentioned serum-free medium was replaced every 4 days thereafter. The serum-free culture supernatant was then collected for purification.

EXAMPLE 3

Purification of Meg-POT from HPC-Y5 Cell Culture Supernatant

After adding Tween 20 at a final concentration of 0.01% to the cell culture supernatant (27.3 liters) of HPC-Y5 cells obtained according to the method described in Example 2, the supernatant was concentrated about 200 fold using the PAN 1200 Artificial Kidney Column (Asahi Medica). The concentrate was dialyzed overnight at 4° C. against 10 mM acetate butler containing 0.01% Tween 20 (pH 5.0). The dialyzed solution was centrifuged (10,000×g, 60 minutes) to remove any insoluble substances, and the supernatant used for the purification described below.

Step 1
S-Sepharose Ion Exchange Chromatography

The above-mentioned centrifuged supernatant was loaded onto an S-Sepharose Fast Flow (Pharmacia) column (5×10 cm) equilibrated with 20 mM acetate buffer (pH 5.0) containing 0.01% Tween 20. After washing the column with the same buffer, the adsorbed protein was eluted while sequentially increasing the concentration of NaCl in the above-mentioned buffer in order from 0.15M to 0.5M and finally 1.0M. After measuring the activity according to the previously described method for the flow-through fraction, washing fraction, and eluted fractions at each salt concentration, Meg-POT activity was observed in the fraction eluted at 0.15M NaCl.

Step 2
DEAE-Sepharose Ion Exchange Chromatography

The active fraction obtained in step 1 was dialyzed overnight at 4° C. with 10 mM Tris-HCl buffer (pH 7.4) containing 0.01% Tween 20, The dialyzed solution was added to a DEAE-Sepharose Fast Flow (Pharmacia) column (2.2×cm) equilibrated with the same buffer, followed by washing the column with said buffer. Adsorbed protein was eluted while sequentially increasing the concentration of NaCl the above-mentioned buffer in order from 0.15M to 0.5M and finally 1.0M. As a result of measuring the activity according to the previously described, method for the flow-through fraction washing fraction and eluted fractions at each salt concentration. Meg-POT activity was observed in the fraction eluted at 0.15M NaCl.

Step 3
Reverse Phase HPLC (I)

After adding 5% trifluoroacetic acid (TFA) to the active fraction obtained in step 2 to adjust the pH to roughly 2, the fraction was loaded onto a reverse phase HPLC column (Protein C4, 10×250 mm, Vydac), and equilibrated with 5% acetonitrile containing 0.1% TFA, at a flow rate of 1.0 ml/minute. Adsorbed protein was eluted at a flow rate of 1.0 ml/minute according to a linear density gradient of acetonitrile (5%→65%, 120 minutes, 0.5% acetonitrile/minute). Detection of the adsorbed protein was performed by monitoring the absorbance at 220 nm and 280 nm. Eluent was fractionated in 1 ml portions. As a result of measuring the activity for each of the fractions, Meg-POT activity was observed in the fraction having an acetonitrile concentration of 40–45%.

Step 4
Reverse Phase HPLC (II)

After diluting the active fraction obtained in step 3 2 fold with 0.1% TFA, the diluted fraction was loaded onto a reverse phase HPLC column (Protein C4, 4.6×250 mm. Vydac), and equilibrated with 35% acetonitrile containing 0.1% TFA, at a flow rate of 1.0 ml/minute. Adsorbed protein was eluted at a flow rate of 1.0 ml/minute according to a linear density gradient of acetonitrile (35%→50%, 75 minutes, 0.2% acetonitrile/minute). Detection of the adsorbed protein was performed by monitoring the absorbance at 220 nm and 280 nm. Eluent was fractionated in 1 ml portions. As a result of measuring the activity for each of the fractions, Meg-POT activity was observed in the fraction having an acetonitrile concentration of 40–45%

Step 5
DEAE-ion Exchange HPLC

After freeze-drying the active fraction obtained in step 4, the freeze-dried fraction was dissolved in 10 mM Tris-HCl buffer (pH 8.0) containing 0.01% Tween 20, and this solution was then loaded onto a Protein Pak G-DEAE column (Waters, 8.2×75 mm), equilibrated with the same buffer, at a flow rate of 0.7 ml/minute. Adsorbed protein was eluted at a flow rate of 0.7 ml/minute according to a linear density gradient of NaCl (0.0M→0.2M, 40 minutes, 5 mM NaCl minute). The eluted protein was detected at 220 nm, and fractionated in 0.7-ml portions. As a result of measuring the activity for each of the fractions, Meg-POT activity was observed in the fraction having a NaCl concentration of 75 mM or less.

Step 6
TSKgel G3000SW Gel Filtration

The active fraction obtained in step 5 was flowed through a TSKgel G3000SW column (21.5×600 nm, guard column 21.5×75 nm, Tosoh), equilibrated with 50 mM Tris-HCl acid buffer (pH 7.4) containing 0.01% Tween 20 and 0.15M NaCl, at a flow rate of 3.0 ml/minute. The eluded protein was detected at 220 nm. As a result of measuring the activity for each of the 3 ml fractions, Meg-POT activity was observed in the fraction having an elution time of 49–54 minutes and that fraction was collected.

Step 7
Reverse Phase HPLC (III)

After adjusting the pH to about 2 by adding 5% TFA, chromatography was performed on the active fraction obtained in step 6 under conditions identical to the reverse phase HPLC (II) of step 4. As a result of measuring the activity for each of the fractions, Meg-POT activity was observed in the main peak (having an acetonitrile concentration of 40–45%). This result is shown in FIG. 1. The main peak indicated with the horizontal bar in FIG. 1 was collected as purified Meg-POT.

EXAMPLE 4

Amino Acid Sequence of Megakaryocyte Potentiator (Meg-POT)

(i) Determination of the N terminal amino acid sequence

Edman degradation was performed on the purified Meg POT sample obtained in Example 3 using the Gas Phase Protein Sequencer Model 470A (Applied Biosystems Inc.). The resulting PTH-amino acids were identified using the PTH Analyzer Model 120 (Applied Biosystems Inc.). As a result, the three types of amino acid sequences indicated below were observed for the amino acid sequences at the N terminal region (sequences 1–3).

TABLE 1

```
                    1               5                   10
Sequence 1  Leu Ala Gly Glu Xaa Gly Gln Glu Ala Ala
                           15
            Pro Leu Asp Gly Val Leu
            (SEQ ID NO: 1; Xaa denotes an unidentified
            amino acid; this notation will be applied
            hereinafter)

1               5                   10
Sequence 2  Ala Gly Glu Thr Gly Gln Glu Ala Ala Pro
                           15
            Leu Asp Gly Val Leu Ala   (SEQ ID NO: 2)

1               5                   10
Sequence 3  Gly Glu Thr Gly Gln Glu Ala Ala Pro Leu Asp
                           15
            Gly Val Leu Ala Asn       (SEQ ID NO: 3)
```

(The numbers indicated above the sequences are the cycle numbers of the Edman degradation)

The amino acid sequence indicated below was observed to be common to the amino acid sequences of 1–3 above.

Gly Glu Thr Gly Gln Glu Ala Ala Pro Leu Asp Gly Val Leu
(SEQ ID NO: 4)

(ii) Digestion with endoproteinase Glu-C

The sample was dissolved in a 0.1M ammonium hydrogencarbonate buffer (pH 7.8), urea and dithiothreitol (DTT) added to give the respective final concentrations of 7.8M and 50 mM, and the mixture incubated at 37° C. for 2 h. To the incubated sample in solution, 0.5 µg of Endo Glu-C (Boehringer-Mannheim) was added and the reaction was carried out at 37° C. for 2 h. Thereafter, an equal volume of the enzyme was added the reaction was carried out a second time at 37° C. for 18 h. To the reaction solution, 10% trifluoroacetic acid (TFA) was added in order to adjust the pH to 2 and thereafter the mixture was loaded onto a 0.1% TFA equilibrated C18 column (4.8×25 cm, Vydac).

For peptide solution, the concentration of acetonitrile in 0.1% TFA was increased linearly from 0 to 64% over 128 min and up to 80% over the subsequent 16 min. Peptides were detected at wavelengths 220 nm and 280 nm. The resulting partially digested peptide fragments were analyzed successively for amino acid sequence using a gas-phase protein sequencer Model 473A (Applied Biosystems, Inc.)

One of the partially digested fragments thus analyzed had the following sequence:

Leu—Ala—Val—Ala—Leu—Ala—Gln—Lys—Asn—Val—Lys—Leu—Ser—Thr—Glu—
Gln—Leu—Arg—Xaa—Leu—Ala—His—Arg—Leu—Ser—Glu—Pro—Pro—Glu—Asp—
Leu—Asp—Ala—Leu—Pro— — —                                          (SEQ ID NO: 5)

EXAMPLE 5

Preparation of Poly(A)$^+$ RNA from HPC-Y5 Cells

The total RNA was prepared from HPC-Y5 cells in accordance with the method described in Chirgwin et al. (Biochemistry, 18, 5294, 1979). Stated specifically, about 1×10⁹ HPC-Y5 cells were homogenized completely in 49 ml of a 5M guanidine thiocyanate (Fulka) solution containing 31.25 mM sodium citrate and 0.625% lauryl sarcosine sodium. The homogenate was layered onto a cushion of 5.3M cesium chloride solution containing 0.1M EDTA in a centrifuge tube, and then centrifuged in a Beckman SW40 rotor at 31,000 rpm for 17 h at 20° C. to precipitate the RNA, The RNA precipitate was washed with 80% ethanol and dissolved in 2.4 ml of a 10 mM Tris-HCl buffer (pH 7.5) containing 1 mM EDTA and 0.5% sodium dodecyl sulfate (SDS). Following the addition of pronase (Boehringer Mannheium) to a final concentration of 0.5 mg/ml, the solution was incubated at 37° C. for 20 min. The RNA solution was deproteinated by treatment with phenol. The residual phenol in the solution was extracted with chloroform and the RNA was thereafter precipitated with ethanol.

Purification of poly(A)⁺ RNA from the total RNA was effected with an mRNA Separator Kit (Clontech Laboratories) consisting of an oligo(dT) cellulose spun column. For higher purity, two purifications were conducted in accordance with the formula attached to the kit.

The above procedure was followed twice to yield purified poly(A)⁺ RNA in the respective amounts of 37 μg and 190 μg.

EXAMPLE 6

Construction of cDNA Library for PCR

Starting with 10 μg of the poly(A)⁺ RNA prepared in Example 5, a double-stranded cDNA was synthesized with the cDNA synthesizing kit c-CLONE (Clontech Laboratories) and thereafter an EcoRI linker was attached to each terminal. The excess unattached EcoRI linkers were removed by agarose gel electro-phoresis and cDNAs longer than 600 bp were recovered by electroelution with a Geneluter (Invitrogen). The linker attached double-stranded cDNA and vector λZAPII (Stratagene) preliminarily treated with EcoRI and alkali phosphatase (Takara Shuzo) were ligated by incubation on 4° C. for 24 h in a 50 mM Tris-HCl buffer (pH 7.5) containing 7 mM magnesium chloride, 1 mM DTT, 1 mM ATP and two units of T4 DNA ligase (Takara Shuzo).

The ligation product was packaged into phage with a Gigapack Gold II packaging extract (Stratagene) and Then transformed so as to construct a cDNA library in HPC-Y5 cells. The library was divided into seven pools (A–G), amplified and recovered into a 50 mM Tris-HCl buffer (pH 7.5) containing 5.8 g/L of sodium chloride, 2 g/L of magnesium sulfate 7 H₂O and 0.01% gelatin.

EXAMPLE 7

Cloning by PCR

Primer T7 of the T7 promoter sequence in the region of the EcoRI site of λZAPII, primer T3-2 of a sequence in the region of T3 promoter, and mix primer N1 containing all codons that were potentially genes coding for the partial amino acid sequence Gly-Glu-Thr-Gly-Gln-Glu-Ala (residues 1–7 of SEQ. ID. NO.:4) in the region of the N terminus of the megakaryocyte potentiator of the present invention were synthesized with a 381A DNA synthesizer (Applied Biosystems).

Further, as shown in Example 4 under (ii), the Endo Glu-C fragment (sequence identification number 5) of the megagaryocyte potentiator of the present invention was found to contain a sequence of codons which have a comparatively low frequency of usage, i.e. the underlined portion of the following sequence (SEQ. ID. NO.:5):

Ala-Gln-Lys-Asn-Val-Lys-Leu-Ser-Thr-Glu-Gln-Leu-Arg-Xaa-Leu-Ala-His-Arg-Leu-Ser-Glu-Pro-Pro-Glu-Asp-Leu-Asp-Ala

Hence, on the basis of this amino acid sequence, mix primers K4S and K4-2A were similarly synthesized so that they contained all base sequences that were potentially genes coding for those amino acids. The base sequences of the primers under consideration are shown below (SEQ. ID. NO.:6–11):

T7:5'-TAATACGACTCACTATAGGG-3'

T3-2:5'-CATGATTACGCCAAGCTCGAA-3'

N1:5'-GG(GATC)GA(GA)AC(GATC)GG(GATC)CA-(GA)GA(GA)GC-3'      (sense)

K4S:5'-GC(GATC)CA(AG)AA(AG)AA(TC)GT(GAT-C)AA(AG)(TC)T-3'      (sense)

K4-2A:5'-GC(GA)TC[(GATC)AG or (TC)AA](AG)TC(TC)TC-(GATC)GG (GATC)GG(TC)TC-3'      (antisense)

To each of the phase suspensions in the seven amplified pools of the cDNA library, pronase, EDTA and SDS were added to give final concentrations of 0.5 mg/ml, 20 mM and 0.5%, respectively, and the resulting mixtures incubated at 37° C. for 1 h. The solutions were deproteinated by treatment with phenol. By subsequent treatment with chloroform, the residual phenol was extracted and the DNA precipitated with ethanol. The thus purified DNA was used as a template for the PCR, and the first stage of the reaction was conducted in a DNA Thermal Cycler (Perkin Elmer Cetus).

The library DNA (500 ng) was amplified in 50 μl of a PCR reaction solution containing 10 mM Tris-HCl buffer (pH 8.3), 50 mM potassium chloride, 1.5 mM magnesium chloride, 0.01% gelatin, 100 μM deoxynucleotide triphosphate (dNTP) and 1 μM each of primers T7 and N1. Following initial denaturation at 95° C. for 7 min, the DNA was cooled to 85° C. and 1.25 units of AmpliTaq DNA polymerase (Perkin Elmer Cetus) was added. Thereafter, PCR was performed through 40 cycles, each cycle consisting of 1 min denaturation at 94° C., 1 min annealing at 60° C., and 2 min elongation at 72° C. Further, one twentieth of the PCR reactive solutions were subjected to the second stage of PCR under the same conditions as stated above using primers K4S and K4-2A.

The solutions which were subjected to the second stage of the PCR were analyzed by 12% polyacrylamide gel electrophoresis and the portion of the gel containing the amplified 84 bp DNA fragments was excised, finely crushed in 500 mM sodium acetate containing 0.1% SDS, 10 mM magnesium acetate and 0.1 mM EDTA, and incubated at 37° C. for 16 h to extract the DNA. The ethanol precipitated DNA was dissolved in 75 μl of 20 mM Tris-HCl buffer (pH 9.5) containing 1 mM spermidine and 0.1 mM EDTA, heated at 90° C. for 2 min and then quenched on ice. Then 10 μl of a 500 mM Tris-HCl buffer (pH 9.5) containing 100 mM 2-mercaptoethanol and 100 mM magnesium chloride, 13 μl of 10 mM ATP and 20 units of polynucleotide kinase (Toyobo) were added and the reaction performed at 37° C. for 1 h in order to phosphorylate the 5' end.

The DNA solutions were deproteinated by treatment with phenol. The residual phenol in the solutions was extracted with chloroform and the DNA precipitated with ethanol. A linearized vector, pSP73 (Promega). That had been treated with restriction enzyme SmaI (Takara Shuzo) and alkaline-phosphatase (Takara Shuzo), was ligated to the resulting DNA sample by incubation at 16° C. for 16 h in 20 μl of a 50 mM Tris-HCl buffer (pH 7.5) containing 7 mM magnesium chloride, 1 mM DTT, 1 mM ATP and 2 units of DNA ligase T4 (Takara Shuzo).

A 10 μl portion of the ligation mixture was added to 100 μl of *E. coli* JM108 competent cells and incubated first on ice for 30 min, then at 42° C. for 1 min and then again on ice for 1 min. Subsequently, 400 μl of SOC medium (Sambrook et al., Molecular Cloning: A Laboratory Manual, Cold Spring Harbor Laboratory Press, 1989) was added. Following incubation at 37° C. for 30 min, the *E. coli* cells were spread on an LB agar medium plate containing 50 μg/ml of ampicillin (Sambrook et al., Molecular Cloning: A laboratory Manual, Cold Spring Harbor Laboratory Press, 1989) and incubated at 37° C. for 16 h to yield *E. coli* transformants.

Five clones of the transformants were each cultured at 37° C. for 16 h in 5 ml of an LB medium containing 50 μg/ml of ampicillin and plasmid DNA from these transformants was prepared from the culture by an alkali lysis procedure (Sambrook et al., Molecular Cloning: A Laboratory Manual, Cold Spring Harbor Press, 1989). The base sequences of the respective inserts were determined with a Sequence Version 2.0 Kit (United States Biochemical) using the dideoxy sequencing procedure. Thereby a 40-bp sequence located between primers K4S and K4-2A was identified (see SEQ ID NO. 29).

On the basis of this base sequence, sense primers 7D-1S (SEQ. ID. NO.:12): 5'-CTCTCAACAGAGCAGCTGCG-3', and 7D-3S (SEQ. ID. NO.;13): 5'-CTGGCTCACCGGCTCTCTGA-3', as well as antisense primers 7D-1A (SEQ. ID. NO.:14): 5'-AGAGCCGGTGAGCCAGACAG-3' and 7D-2A (SEQ. ID. NO:15): 5'-GCGCAGCTGCTCTGTTGAGA-3' were synthesized. Under the same conditions as described above, the cDNA library was used as a template, and the first stage of the PCR was conducted using primers T7 and 7D-1S in combination, and also primers T3-2 and 7D-1A in combination. The second stage of the PCR was then conducted using primers T7 and 7D-3S in combination and also primers T3-2 and 7D-2A in combination.

The PCR products were analyzed by electrophoresis in a 1% agarose gel and the portion of the gel containing the desired amplified DNA fragments was excised, and the DNA extracted with a Sephaglas BandPrep Kit (Pharmacia). The base sequence of the extracted DNAs was directly determined using a fmol DNA Sequencing System (Promega). The portion of the genes coding for the megakaryocyte potentiator of the present invention was verified as shown in SEQ ID NOS. 30 and 31.

On the basis of this base sequence, sense primer 3AS1 (SEQ. ID. NO.:16): 5'-AACTCCTTGGCTTCCCGTGTG-3' and antisense primer 7SA1(SEQ. ID. NO.:17): 5'-CGCATCTGGGTTGAGGAATAG-3' were synthesized and a PCR was conducted on pool D under the conditions specified above. Thereby, a 197 bp DNA fragment (SEQ ID NO. 32) was amplified. The amino acid sequence encoded by this DNA fragment agreed with the amino acid sequence that was determined using the purified Meg-POT of Example 3. This DNA fragment (Q197A) was then used as a probe for subsequent screening.

EXAMPLE 8

Screening of cDNA Library with Probe Q197A

Starting with 5 μg of the poly(A)⁺ RNA prepared in Example 5, a double-stranded cDNA was synthesized with a ZAP-cDNA Synthesis Kit (Stratagene) and ligated to the arm of vector λZaPII (Stratagene). The ligation product was packaged with a Gigapack gold II packaging extract (Stratagene) and transformed into HPC-Y5 cells in order to construct a second cDNA library.

The PCR amplified 197 bp DNA (Example 7) was subjected to acrylamide gel electrophoresis and then recovered from the gel. The recovered DNA fragment Q197A was $^{32}$P-labelled with a random primer DNA labelling kit (Takara Shuzo), however, instead of the attached random primer, primers 3AS1 and 7SA1 were used at a concentration of 400 nM for the labelling reaction. The unincorporated dNTP was removed by passage through a NICK-Column (Pharmacia). Subsequently, plaque hybridization was performed in accordance with the method of Benton and Davis (Science, 196, 180, 1977).

When phase plaques formed on an agar medium, a Hybond-N+ filter (Amersham) was placed on the medium such that the phage were transferred onto the filter. The filters were then treated using the following procedure. First, the DNA bound to the filters was denatured in an aqueous solution of 0.5N sodium hydroxide containing 1.5M sodium chloride for 5 min. Thereafter, the filters were soaked in an aqueous solution of 0.1N sodium hydroxide containing 1.5M sodium chloride for 1 min, and then soaked twice in 0.5M Tris-HCl buffer (pH 7.4) containing 1.5M sodium chloride for 1 min each time. Finally, the filters were soaked in 2× SSCP (240 mM NaCl, 30 mM Na₃ citrate, 26 mM KH$_2$PO$_4$, and 2 mM EDTA) for 1 min.

In the next step, the filter was dried and soaked in an aqueous solution of 0.4N sodium hydroxide for 20 min, then soaked twice in 5× SSPE (Sambrook et al., Molecular Cloning: A Laboratory Manual, Cold Spring Harbor Laboratory Press, 1989) for one minute each time. The filter was then incubated at 42° C. for 4 h in a prehybridization solution containing 50% formamide, 5× SSPE, 5× Denhardt's solution (Sambrook et al., Molecular Cloning: A Laboratory Manual, Cold Spring Harbor Laboratory Press, 1989), 0.1% SDS and 0.1 mg/ml denatured salmon sperm DNA (Boehringer Mannheim).

Hybridization was conducted at 42° C. for 16 h in a hybridization solution [50% formamide, 5× SSPE, 5× Denhardt's solution, 0.1 mg/ml denatured DNA (salmon sperm DNA) and 0.1% SDS] that contained the probe Q197A labelled in the manner described above. Following hydrization, the filter was washed twice, for 1 h each time, with 2× SSC containing 0.05% SDS at room temperature, then washed twice, for 1 h each time, with 1× SSC containing 0.1% SDS at 68° C., and finally washed for 1 h with 0.2× SSC containing 0.1% SDS at 68° C. Thereafter, the radio-labelled DNA was detected by autoradiography.

Figure 2:
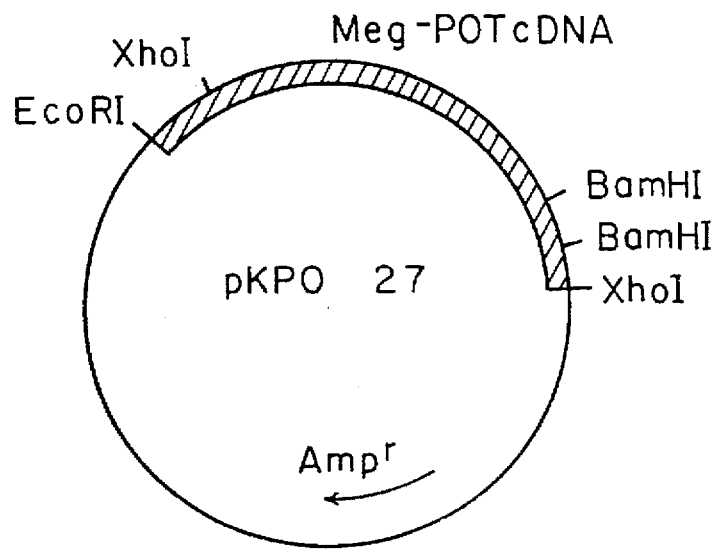
FIG. 2 shows the structure of plasmid pKPO27.

As a consequence of the procedure described above, 23 positive phase clones were obtained. Among them, those clones which were believed to contain full-length cDNAs were subcloned into plasmids using helper phage R408 in accordance with the instructions attached to a ZAP-cDNA Synthesis Kit (Stratagene). Of the two plasmids obtained, the base sequence of the cloned DNA of pKPO27 (FIG. 2) was determined by the dideoxy sequencing method using a Sequenase Version 2.0 Kit (United Stated Biochemical). The base sequence of the cloned pKPO27 DNA, is shown as SEQ ID NO. 34. The base sequence of the cloned DNA of the other plasmid pKPO21 was also determined by the same method and it was shown that the G (guanine) in position 1873 of the base sequence shown as SEQ ID NO. 34 was changed to A (adenine) [therefore, the Val (valine) in position 593 accordingly changed to Met (methionine)], however the remainder of the sequence was identical to that of pKPO27.

The data base Gen Bank Re. 1.71 was searched for these base sequences, and the amino acid sequences encoded by them, and the novelty thereof confirmed.

E. Coli containing the plasmid pKPO27 was deposited internationally as Escherichia coli JM109 (pKPO27) under FERM BP-4029, at the Fermentation Research Institute, Agency of Industrial Science and Technology (1-3, Higashi 1-chome, Tsukuba City, Ibaraki, Japan) under the terms of the Budapest Treaty on Oct. 12, 1992. In the same manner, E. coli containing the plasmid pKPO21 was deposited the deposition number is FERM BP-4071 and the date of deposition is Nov. 10, 1992.

EXAMPLE 9

Construction of Vector pRVHKPO27 (for Animal Cells)

Plasmid pKPO27 obtained An Example 8 was digested with restriction enzyme EcoRI (Takara Shuzo) at 37° C. for 2 h in a 20 mM Tris-HCl buffer (pH 7.5) containing 10 mM $MgCl_2$, 1 mM DTT and 100 mM NaCl and thereafter the digested DNA recovered as a precipitate in ethanol. The recovered DNA was further digested with restriction enzyme BamHI (Takara Shuzo) at 37° C. for 2 h in a 20 mM Tris-HCl buffer (pH 8.5) containing 10 mM $MgCl_2$, 1 mM DTT and 100 mM KCl, and then resolved by agarose gel electrophoresis in order to recover a 1.8 kbp DNA fragment.

Vector HEF-12h-gγ1 was likewise digested with restriction enzymes EcoRI and BamHI; thereafter, alkalinephosphatase (Takara Shuzo) was added and the reaction solution incubated at 65° C. for 2 h to effect dephosphorylation. By agarose gel electrophoresis, 8.7 kbp DNA fragment was recovered and then mixed with the previously obtained 1.8 kbp DNA fragment. The DNA fragments were then ligated with T4 DNA ligase overnight at 16° C. in a 66 mM Tris-HCl buffer (pH 7.5) containing 6.6 mM $MgCl_2$, 5 mM DTT and 1 mM ATP. The ligation product was transformed into E. coli strain JM109 in order to construct pRVHKPO27 (FIG. 3).

Figure 3:
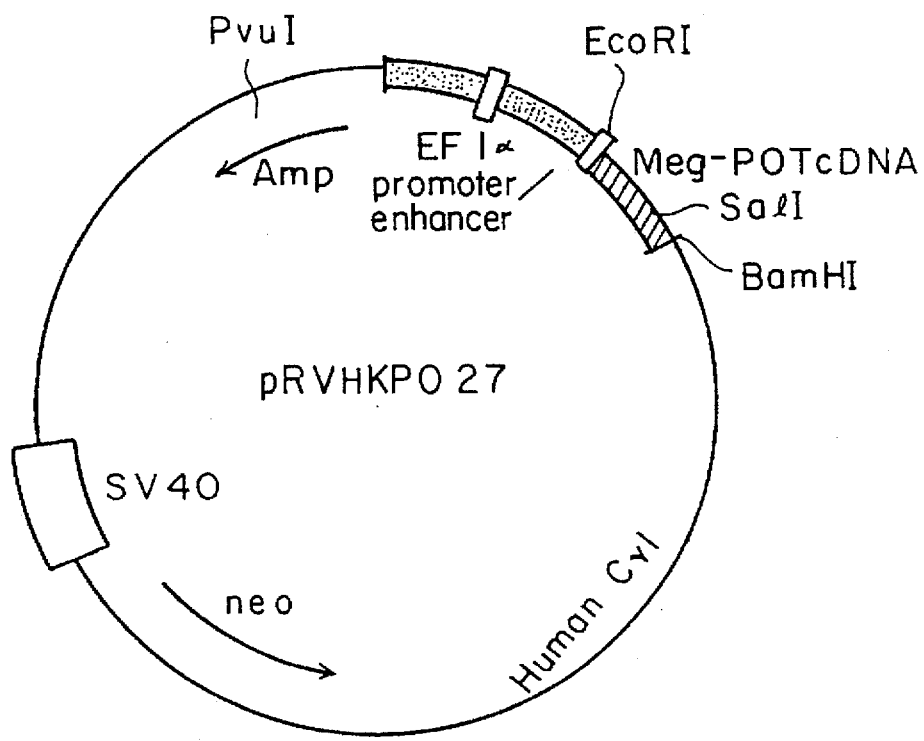
FIG. 3 shows the structure of plasmid pRVHKPO27.

As shown in FIG. 3, the plasmid pRVHKPO27 contains the EFIα promoter, gene for the constant domain of the H chain of human immunoglobulin, SV40 enhancer promoter, replication initiation region derived from pBR322 and β-lactamase gene. (Amp$^r$), and a portion of the human Meg-POT cDNA inserted between the EFIα promoter and the gene for the constant domain of the H chain of human immunoglobulin.

Vector HEF-12h-gγ1 was prepared by the following procedure. The 2.5-kbp HEF-1α promoter-enhancer region, which is a constituent element of vector HEF-12th-gγ1, consists of ca. 1.5-kbp DNA derived from the 5'-terminus of the gene, 33 bp of the first exon, 943 bp of the first intron, and 10 bp of the second exon. This 2.5 kbp HindIII-EcoRI fragment was originally cleaved from plasmid pEF321-CAT (D. W. Kim et al., Gene, 91, 217, 1990; and T. Uetsuki et al., J. Biol. Chem., 264, 5791, 1989) inserted into vector pdKCR (M. Tsuchiya et al., Embo. J., 6, 611, 1987; K. O'Hara et al., Proc. Natl. Acad. Sci., U.S.A., 78, 1527, 1981; and R. Fukunaga et al., Proc. Natl. Acad. Sci., U.S.A., 81, 5086, 1984), and a portion thereof was then replaced with a ca. 300 bp HindIII-EcoRI fragment containing the SV40 prophase promoter-enhancer, thereby yielding pTEF-1.

The vector pTEF-1 was digested with EcoRI, filled in with Klenow polymerase, ligated to HindIII linkers, and digested with SmaI. Subsequently, a HindIII-SmaI fragment of ca. 1.6 kbp was recovered from the DNA of the modified vector DTEF-1.

HCMV-12h-gγ1 (Maeda et al., Human Antibodies and Hybridomas, 2, 124, 1991; C. A. Kettleborough et al., Protein Engineering, 4, 773, 1991) was digested partially with EcoRI, filled in with Klenow polymerase and selfligated to construct plasmid HCMV-12h-gγ1 (ΔE2) from HCMV-12h-gγ1.

Plasmid HCMV-12h-gγ1 (ΔE2) was digested with EcoRI, filled in with Klenow polymerase and digested with HindIII. A ca. 7 kbp fragment containing a DNA sequence coding for the human α-IC region was ligated to the above-mentioned 1.6 kbp HindIII-SmaI fragment containing the HEF-1α promoter-enhancer, thereby yielding HEF-12h-gγ1. The HEF-1α promoter-enhancer enhancer region of this vector is identical to that of pTEF-1, except for 380 bp located in the 5'-region thereof.

EXAMPLE 10

Expression I of the Megakaryocyte Potentiator (Meg-POT) Gene in COS Cells

COS cells were suspended in PBS to give a concentration of $1\times10^7$ cells/ml and 10 µg of pRVHKPO27 was added to 0.8 ml of the resulting cell suspension. The plasmid was introduced into the COS cells by electroporation with a GenePulsar electroporator (BioRad) under the following conditions: 1,900 V, 25 µF and 0.4 msec. Following a 10 min recovery period at room temperature, the electroporated cells were added to 25 ml of Dulbecco's Minimum Essential medium (DMEM) (Gibco) containing 1% fetal bovine serum allowed to grow for 72 h, and thereafter the supernatant of the cell culture was collected.

Part of the thus obtained supernatant of the COS cell culture was concentrated approximately 10 fold with a Centriprep-10 filter (Amicon) and assayed by SDS/PAGE. As controls, the supernatant of the culture of untreated COS cells and that of COS cells into which only the vector was introduced, were likewise concentrated approximately 10 fold and subjected to electrophoresis. The gel concentration was 12% and the electrophoresis was conducted in accordance with the method of Laemmli (Nature, 227, 680, 1970), and one gel containing the electrophoresed samples was stained for protein with 2D-silver staining reagent II "Dai-ichi" (Dai-ichi Kagaku Yakuhin).

The molecular weight markers were of a low-molecular weight type obtained from BioRad [phosphorylase B (92.5 kd), bovine serum albumin (66.2 kd), ovalbumin (45.0 kd), carbonic anhydrase (31.0 kd), soybean trypsin inhibitor (21.5 kd) and lysozyme (14.4 kd)].

The other gel containing the duplicate electrophoresed samples was used to assay for the megakaryocyte potentiator by the Western blot technique. The prestained molecular weight markers used in this case were obtained from BioRad [phosphorylase B (106.0 kd), bovine serum albumin (80.0 kd), ovalbumin (49.5 kd), carbonic anhydrase (32.5 kd), soybean trypsin inhibitor (27.5 kd), and lysozyme (18.5 kd)]. The primary antibody was a polyclonal antibody that was prepared by immunizing rabbits with an antigenic peptide of 18 residues that had been synthesized on the basis of the sequence obtained from N-terminal sequence analysis of the megakaryocyte potentiator purified from the supernatant of the culture of HPC-Y5.

The silver stained bands were compared between the sample and each of the two controls; the band occurring at a molecular weight of ca. 33,000 was found only in the supernatant of the culture of COS cells into which the megakaryocyte potentiator gene had been introduced. Intense staining occurred only in the band having the mol. wt. ca. 33,000 when assayed by the Western blot technique. It was therefore assumed that this band represented a recombinant megakaryocyte potentiator.

EXAMPLE 11

Measurement I of the Activity of Megakaryocyte Potentiator (Meg-POT) in The Supernatant of the Culture of COS Cells The activity of the megakaryocyte potentiator in the supernatant of the culture of COS cells which was obtained in Example 10 was measured by the method described hereinabove. Since it is known that IL-6 is induced in the supernatant of the culture of COS cells resulting from stimulation from the introduction of genes into the COS cells, the measurement of activity was conducted in a system incorporating an antibody against a mouse IL-6 receptor.

The results are shown in Table 2 below. Neither the supernatant of the culture of untreated COS cells, into which no genes were introduced, nor the supernatant of the culture of control COS cells having incorporated therein a vector free from the cDNA of Meg-POT, exhibited the megakaryocyte potentiator activity. On the other hand, the supernatant of the culture of COS cells having incorporated therein a vector containing the cDNA of Meg-POT clearly exhibited the megakaryocyte potentiator activity.

TABLE 2

| Megakaryocyte Potentiator Activity in the Supernatant of the Culture of COS Cells | | | | |
|---|---|---|---|---|
| COS cells | % Concentration of activity in COS cell culture | Megakaryocyte potentiator activity[a] | | |
| | supernatant | 50 | 0.5 | 0.005 |
| Untreated COS | | 1.5 | 3 | ND[b] |
| Control COS | | 0 | 2.5 | ND |
| Meg-POT cDNA harboring COS | | 8.5 | 7 | 3.5 |

[a] The number of colonies formed minus the number of colonies (28.5) formed in the presence of IL-3 alone.
[b] Not measured.

EXAMPLE 12

Purification I of Recombinant Megakaryocyte Potentiator (Meg-POT) from the Supernatant of the Culture of COS Cells To 350 ml of the supernatant of the culture of COS cells obtained in Example 10, Tween 20 was added to give a final concentration of 0.01% and the supernatant was concentrated about 10 fold by ultrafiltration using an Amicon PM-10 filter (Amicon). A recombinant megakaryocyte potentiator (Meg-POT) was purified from the liquid concentrate by the following procedure.

(i) The concentrated supernatant was dialyzed overnight at 4° C. against 10 L of a 10 mM Tris-HCl buffer (pH 8.4) containing 0.01% Tween 20. Thereafter, the dialyzed solution was loaded onto a DEAE-Sepharose fast flow column (2.2×18 cm, Pharmacia) that had been equilibrated with the same buffer. After washing the column with the same buffer, the NaCl concentration was raised stepwise In order from 0 to 0.1, 0.15, 0.2 and finally 0.5M in the same buffer, so as to elute the proteins absorbed on the column. Analysis by SDS/PAGE of the factions thus obtained showed that the band with a molecular weight of about 33,000, as observed in Example 10, was detected only in the first half of the fraction having a NaCl concentration of 0.1M. This fraction was collected and purified in the subsequent step by reverse-phase HPLC.

(ii) The 0.1M fraction was mixed with 10% TFA in order to adjust the pH to 3 or below, and then the mixture was loaded on a Vydac C4 column (4.6×250 mm) that had been equilibrated with 24% acetonitrile containing 0.1% TFA. The column was washed with the same eluting solution and thereafter, the concentration of acetonitrile in 0.1% TFA was raised linearly from 24 to 64% over 80 min, then up to 80% over the subsequent 10 min, thereby eluting the proteins adsorbed on the column. The flow rate was ca. 1.0 ml/min and protein detection was conducted at wavelengths 220 nm and 280 nm. The peaks attained were analyzed by SDS/PAGE and a band with a molecular weight of ca. 33,000 was detected at an acetonitrile concentration of ca. 41%. This fraction was diluted with 0.1% TFA and subjected to another cycle of reverse-phase HPLC under the same conditions, thereby recovering the main peak.

EXAMPLE 13

Amino Acid Sequence Analysis of the Recombinant Megakaryocyte Potentiator (Meg-POT)

The N-terminal amine acid sequences of the recombinant Meg-POT of Example 12 were analyzed by means of a gas-phase protein sequencer Model 473A (Applied Biosystems). As a result, three N-terminal amino acid sequences as listed below under (a), (b) and (c) were identified, verifying that the band with a molecular weight of ca. 33,000 as identified in Example 10, is the recombinant megakaryocyte potentiator (SEQ. ID. NO.:1):

(a) Ser—Arg—Thr—Leu—Ala—Gly—Glu—Thr—Gly—Gln—Glu—Ala—Ala—Pro— (SEQ ID NO. 11)
Leu—Asp— — —

(b) Leu—Ala—Gly—Glu—Thr—Gly—Gln—Glu—Ala—Ala—Pro—Leu—Asp—Gly—
Val—Leu—Ala—Asn—Pro—Pro—Xaa—Ile—Ser—Xaa—Leu—Xaa—Pro—Arg—
— —

-continued (c) Gly—Glu—Thr—Gly—Gln—Glu—Ala—Ala—Pro—Leu—Asp—Gly—Val—Leu—
Ala—Asn—Pro—Pro—Xaa—Ile—Ser—Xaa—Leu—Xaa—Pro—Arg—Gln—Leu—

Of these amine acid sequences, (b) and (c) correspond, respectively, to polypeptide sequence 1 and sequence 3 (SEQ ID NO. 3) obtained from the supernatant of the culture of HPC-Y5 cells, as prepared in Example 4 under (i).

A solution of 70% formic acid (100 μl) containing 10 mg/ml of cyanogen bromide was added to the recombinant Meg-POT and cyanogen bromide cleavage was effected at room temperature for 24 h. Thereafter, excess reagents were removed by means of a centrifugal concentrator. The residue was dissolved in 1 ml of 0.1% TFA and loaded on a Vydac C4 column (4.6×250 mm) equilibrated with 0.1% TFA. The concentration of acetonitrile in 0.1% TFA was raised linearly up to 804 over 40 min. whereby the cyanogen bromide fractions adsorbed on the column were eluted. The C-terminal portion of the fragments was sequenced using a gas-phase protein sequencer Model 473A. The sequence thus identified is shown below, and therein one can see that the sequence agrees with a partial sequence of the cyanogen bromide fragment obtained by performing a similar cyanogen bromide cleavage on the megakaryocyte potentiator (Meg-POT) that was isolated from The supernatant of the cultures HPC-Y5 (SEQ. ID. NO.:19).

recovered DNA was then digested with restriction enzyme SalI (Toyobo) at 37° C. for 2 h in a 50 mM Tris-HCl buffer (pH 7.5) containing 10 mM MgCl$_2$, 1 mM DTT and 100 mM NaCl, followed by agarose gel electrophoresis to recover a 1.3 kbp DNA fragment.

Vector pRVHKPO27 which was prepared in Example 9 was digested with restriction enzyme BamHI (Takara Shuzo) at 37° C. for 2 h in a 20 mM Tris HCl buffer (pH 8.5) containing 10 mM MgCl$_2$, 1 mM DTT and 100 mM KCl and the digested DNA recovered as a precipitate in ethanol. The recovered DNA was further treated with the Klenow fragment of DNA polymerase at 10° C. for 1 h in a 20 mM Tris-HCl buffer (pH 7.4) containing 5 mM MgCl$_2$, 10 mM DTT and 1 mM each of dATP, dCTP, dGTP and dTTP, and thereby blunt ends were created.

The resulting DNA was recovered as a precipitate in ethanol. The recovered DNA was subsequently digested with restriction enzyme SalI (Toyobo) at 37° C. for 2 h in a 50 mM Tris-HCl buffer (pH 7.5) containing 10 mM MgCl$_2$, 1 mM DTT and 100 mM NaCl. Thereafter, alkaline phosphatase (Takara Shuzo) was added and the reaction solution was incubated at 85° C. for 2 h to effect dephosphorylation.

TABLE 3

|  | 5 | 10 | 15 | 20 |
|---|---|---|---|---|
| cDNA | :Asp—Ala—Leu—Arg—Gly—Leu—Leu—Pro—Val—Leu—Gly—Gln—Pro—Ile—Ile—Arg—Ser—Ile—Pro—Gln— | | | |
| COS | :Asp—Ala—Leu—Arg—Gly—Leu—Leu—Pro—Val—Leu—Gly—Gln—Pro—Ile—Ile—Arg—Ser—Ile—Pro—Gln— | | | |
| HPC-Y5 | :Asp—Ala—Leu—Arg—Gly—Leu—Leu—Pro—Val—Leu—Gly—Gln—Pro—Ile—Ile— ... | | | |
|  | 25 | 30 | 35 | 40 |
| cDNA | :Gly—Ile—Val—Ala—Ala—Trp—Arg—Gln—Arg—Ser—Ser—Arg—Asp—Pro—Ser—Trp—Arg—Gln—Pro—Glu— | | | |
| COS | :Gly—Ile—Val—Ala—Ala—Trp—Arg—Gln—Arg—Ser—Ser—Xaa—Asp—Pro—Xaa—Trp—Xaa—Gln— ... | | | |

The amino acid sequence for "cDNA" is the sequence deduced from the base sequence of cDNA coding for the Meg-POT; the amino acid sequence for "COS" is a partial sequence obtained by performing amino acid sequence analysis on the protein expressed in COS cells by the cDNA coding for the Meg-POT; and the amino acid sequence for "HPC-Y5" is a partial sequence obtained by performing amino acid sequence analysis on the Meg-POT produced from the supernatant of the "HPC-Y5" culture, or cloned cells derived from human pancreatic cancer cells.

EXAMPLE 14

Construction of Vector pRVHKPO27f (for Animal Cells)

Plasmid pKPO27 obtained in Example 8 was treated with restriction enzyme XhoI (Toyobo) at 87° C. for 2 h in a 50 mM Tris-HCl buffer (pH 7.5) containing 10 mM MgCl$_2$, 1 mM DTT and 100 mM NaCl and DNA was recovered as a precipitate in ethanol. The recovered DNA was further treated with the Klenow fragment of DNA polymerase at 10° C. for 1 h in a 20 mM Tris-HCl buffer (DH 7.4) containing 5 mM MgCl$_2$, 10 mM DTT, 1 mM each of dATP, dCTP, dGTP and dTTP, and thereby blunt ends were created. The resulting DNA was recovered as a precipitate in ethanol. The By agarose gel electrophoresis, an 8.5 kbp DNA fragment was recovered. This 8.5 kbp DNA fragment was mixed with the previously obtained 1.3 kbp DNA fragment and the mixture reacted with T4 DNA ligase overnight at 16° C. in a 66 mM Tris-HCl buffer (pH 7.5) containing 6.6 mM MgCl$_2$, 1 mM DTT and 5 mM ATP. The ligation product was introduced into *E. coli* strain JM109 in order to construct pRVHKPO27f (FIG. 4).

Figure 4:
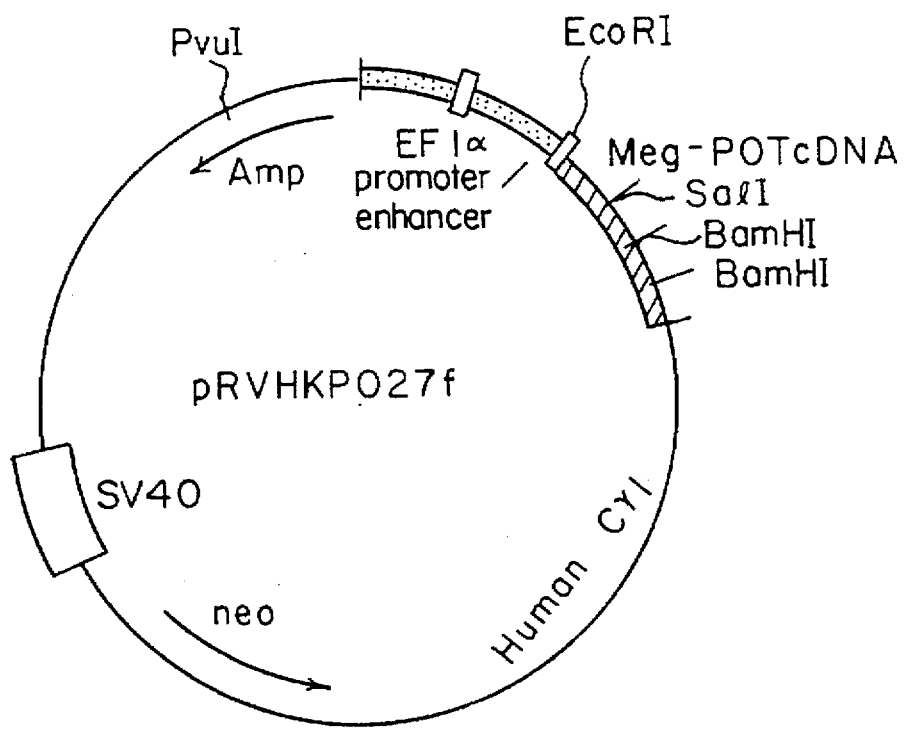
FIG. 4 shows the structure of plasmid pRVHKPO27f.

As shown in FIG. 4, the plasmid pRVHKPO27f contained EF1α promoter, gene for the constant domain of the H chain of human immunoglobulin, SV40 enhancer promoter, replication initiation region derived from pBR322 and β-lactamase gene (Amp$^r$), and the human Meg-POT cDNA inserted between the EF1α promoter and the gene for the constant domain of the H chain of human immunoglobulin.

EXAMPLE 15

Expression II of Megakaryocyte Potentiator (Meg-POT) Gene in COS Cells

COS cells were suspended in PBS to give a concentration of 1×10$^7$ cells/ml and 10 μg of pRVHKPO27f was added to 0.8 ml of the resulting cell suspension. The plasmid was introduced into the COS cells by electroporation with a GenePulsar (BioRad) at 1,900 V, 25 μF for 0.4 msec.

Following a 10 min recovery period at room temperature, the electroporated cells were added to 25 ml of Dulbecco's Minimum Essential Medium (DMEM) (Gibco) containing 1% fetal bovine serum. After growing for 72 h, the supernatant of the culture was collected.

Part of the thus obtained supernatant of the culture of COS cells was concentrated about 10 fold with a Centriprep-10 filter (Amicon) and assayed by SDS/PAGE. As a control, the supernatant of the culture of COS cells, into which only the vector was introduced, was likewise concentrated about 10 fold and subjected to electrophoresis. The gel concentration was 12% the electrophoresis was conducted in accordance with the method of Laemmli (Nature, 227, 680, 1970), and one gel containing the electrophoresed samples was stained for protein with 2D-silver staining reagent II "Dai-ichi" (Dai-ichi Kagaku Yakuhin). 2D-silver staining reagent II "Dai-ichi" is a kit comprising a thiourea fixing agent, a pre-treating agent composed of dithiothreitol, glutaraldehyde and thiourea, a first staining solution that is a silver nitrate solution, a second staining solution that is composed of ammonium hydroxide and sodium hydroxide, a developing solution that is composed of citric acid, formaldehyde and sodium thiosulfate and a stop solution composed of citric acid.

The molecular weight marker was of a low-molecular weight type obtained from BioRad [phosphorylase B (92.5 kd), bovine serum albumin (66.2 kd), ovalbumin (45.0 kd), carbonic anhydrase (31.0 kd), soybean trypsin inhibitor (21.5 kd) and lysozyme (14.4 kd)].

The other gel containing the duplicate electrophoresed samples was used to assay for the megakaryocyte potentiator by the Western blot technique. The prestained molecular weight markers used in this case were obtained from BioRad [phosphorylase B (106.0 kd), bovine serum albumin (80.0 kd), ovalbumin (49.5 kd), carbonic anhydrase (32.5 kd), soybean trypsin inhibitor (27.5 kd) and lysozyme (18.5 kd)]. The primary antibody was a polyclonal antibody that was prepared by immunizing rabbits with an antigenic peptide of 18 residues that had been synthesized on the basis of the sequence obtained from N-terminal sequence analysis of the megakaryocyte potentiator purified from the supernatant of the culture of HPC-Y5.

The silver stained bands were compared between the sample and the control; the band occurring at a molecular weight of ca. 33,000 was found only in the supernatant of the culture of COS cells into which the megakaryocyte potentiator gene had been introduced. Intense staining occurred only In the band having the mol. wt. 33,000 when assayed by the Western blot technique. It assumed therefore assumed that this band represented a recombinant megakaryocyte potentiator.

EXAMPLE 16

Measurement II of the Activity of Megakaryocyte Potentiator (Meg-POT) in the Supernatant of the Culture of COS Cells The activity of the megakaryocyte potentiator in the supernatant of the culture of COS cells which was obtained in Example 15 was measured by the method described hereinabove. Since it is known that IL-6 is induced in the supernatant of the culture of COS cells resulting from stimulation from the introduction of genes into the COS cells, the measurement of activity was conducted in a system incorporating an antibody against a mouse IL-6 receptor.

The results are shown in Table 4 below. Neither the supernatant of the culture of the untreated COS cells into which no genes were introduced, nor the supernatant of the culture of control COS cells having incorporated therein a vector free from the cDNA of Meg-POT, exhibited the megakaryocyte potentiator activity. On the other hand, the supernatant of the culture of COS cells having incorporated therein a vector containing the cDNA of Meg-POT clearly exhibited the megakaryocyte potentiator activity.

TABLE 4

| | Megakaryocyte Potentiator Activity in the Supernatant of the Culture of COS Cells | | | | |
|---|---|---|---|---|---|
| | | % Concentration of activity in COS cell culture | Megakaryocyte potentiator activity[a] | | |
| COS cells | supernatant | 2 | 0.2 | 0.02 | 0.002 |
| Untreated COS | | 0 | ND[b] | ND | ND |
| Control COS | | 2 | ND | ND | ND |
| Meg-POT cDNA harboring COS | | 7 | 4 | 7 | 1 |

[a] The number of colonies formed minus the number of colonies (10) formed in the presence of IL-3 alone.
[b] Not measured.

EXAMPLE 17

Purification II of Recombinant Megakaryocyte Potentiator (Meg-POT) from the Supernatant of the Culture of COS Cells To 350 ml of the supernatant of the culture of COS cells obtained in Example 15, Tween 20 was added to give a final concentration of 0.01% and the supernatant was concentrated about 10 fold by ultrafiltration using an Amicon PM-10 filter (Amicon). A recombinant megakaryocyte potentiator (Meg-POT) was purified from the liquid concentrate by the following procedure.

(i) The concentrated supernatant was dialyzed overnight at 4° C. against 10 L of a 10 mM Tris-HCl buffer (pH 8.4) containing 0.01% Tween 20. Thereafter, the dialyzed solution was loaded on a DEAE-Sepharose fast flow column (2.2×18 cm. Pharmacia) that had been equilibrated with the same buffer. After washing the column with the same buffer, the NaCl concentration was raised stepwise in order from 0 to 0.1, 0.15, 0.2 and finally 0.5M in the same buffer so as to elute the proteins adsorbed on the column. Analysis by SDS/PAGE of the fractions obtained showed that the band with a molecular weight of about 33,000 as observed in Example 15, was detected in the fraction having a NaCl concentration of 0.1M. This fraction was then subjected to purification by reverse-phase HPLC.

(ii) The 0.1M fraction was mixed with 10% TFA in order to adjust the pH to 3 and below and then the mixture was loaded on a Vydac C4 column (4.6×250 mm) that had been equilibrated with 24% acetonitrile containing 0.1% TFA. The column was washed with the same eluting solution and thereafter, the concentration of acetonitrile in 0.1% TFA was raised linearly from 24 to 64% over 80 min, then up to 80% over the subsequent 10 min, thereby eluding the proteins adsorbed on the column. The flow rate was ca. 1.0 ml/min and protein detection was conducted at wavelengths 220 nm and 280 nm. The peaks attained were analyzed by SDS/PAGE and a band with a molecular weight of ca. 33,000 was detected at an acetonitrile concentration of ca. 41%. This fraction was diluted with 0.1% TFA and subjected to another cycle of reverse-phase HPLC under the same conditions, thereby recovering the main peak.

EXAMPLE 18

Measuring the Activity of Purified Recombinant Meg-POT

A test sample (0.1 ml), or the recombinant megakaryocyte potentiator (Meg-POT) that was purified in Example 17 and which was diluted to a predetermined concentration (50.1, 3.1 or 0.2 ng/ml) with Iscove's modified Dulbecco's medium (IMDM) containing 10% equine serum, was mixed with 0.2 ml of equine serum (preheated to 56° C. for 30 min, Biocell), 0.1 ml of mouse femoral myeloid cell suspension ($2 \times 10^5$ nucleated cells derived from 6–12 week old C57BL/6N male mice), 0.2 ml of IMDM containing 5 ng/ml of recombinant mouse IL-3 and 0.4 ml of modified McCoy's 5A medium containing 0.75% agar. Subsequently, the mixture was placed in a plastic tissue culture dish of 35 mm in diameter and allowed to solidify. Thereafter, a culture was grown at 37° C. in 5% $CO_2$/95% air, and 100% humidity.

On the 6th day of culturing, the entire agar layer was moved onto a glass slide and allowed to dry. The film-like specimens were then fixed with 5% glutaraldehyde, followed by staining with acetylcholinesterase in order to determine the number of megakaryocyte colonies in accordance with the method of Nakeff (Proc. Soc. Exp. Biol. Med., 151, 587, 1976). When counting colonies, clumps of cells containing 4 or more acetylcholinesterase positive cells are defined as megakaryocyte colonies (note, the colonies were examined at a magnification of 4×).

The measure of the megakaryocyte potentiator activity was defined as the difference between the number of megakaryocyte colonies that formed upon addition of the recombinant Meg-POT and the number of megakaryocyte colonies that formed in the presence of recombinant IL-3 alone without addition of the recombinant Meg-POT (and adding only IMDM containing 10% equine serum).

As Table 5 shows, the purified recombinant Meg-POT exhibited the megakaryocyte potentiator activity.

TABLE 5

Megakaryocyte Potentiator Activity of Purified Recombinant Meg-POT

| Meg-POT concentration, ng/ml[a] | Megakaryocyte potentiator activity[b] |
|---|---|
| 50.1 | 9.5 |
| 3.1 | 8.5 |
| 0.2 | 3 |

[a] Measured by amino acid analysis.
[b] The number of colonies formed minus the number of colonies (19.5) formed in the presence of IL-3 alone.

EXAMPLE 19

In Vitro Transcription and Translation of Genes Coding for Megakaryocyte Potentiator (Meg-POT)

Plasmid DKPO27 obtained in Example 8 was digested with restriction enzyme XhoI (Toyobo) at 37° C. for 2 h in a 20 mM Tris-HCl buffer (pH 8.5) containing 10 mM $MgCl_2$, 1 mM DTT and 100 mM KCl. By subsequent agarose gel electrophoresis, a 1.9 kbp DNA fragment was recovered.

In a separate step, vector pCITE-2c (Novagen) was digested with restriction enzyme XhoI (Toyobo) at 37° C. for 2 h in a 20 mM Tris-HCl buffer (pH 8.5) containing 10 mM $MgCl_2$, 1 mM DTT and 100 mM KCl. Thereafter, alkaline phosphatase (Takara Shuzo) was added and the reaction solution was incubated at 65° C. for 2 h to effect dephosphorylation. The resulting DNA was purified by treatment with phenol.

Figure 5:
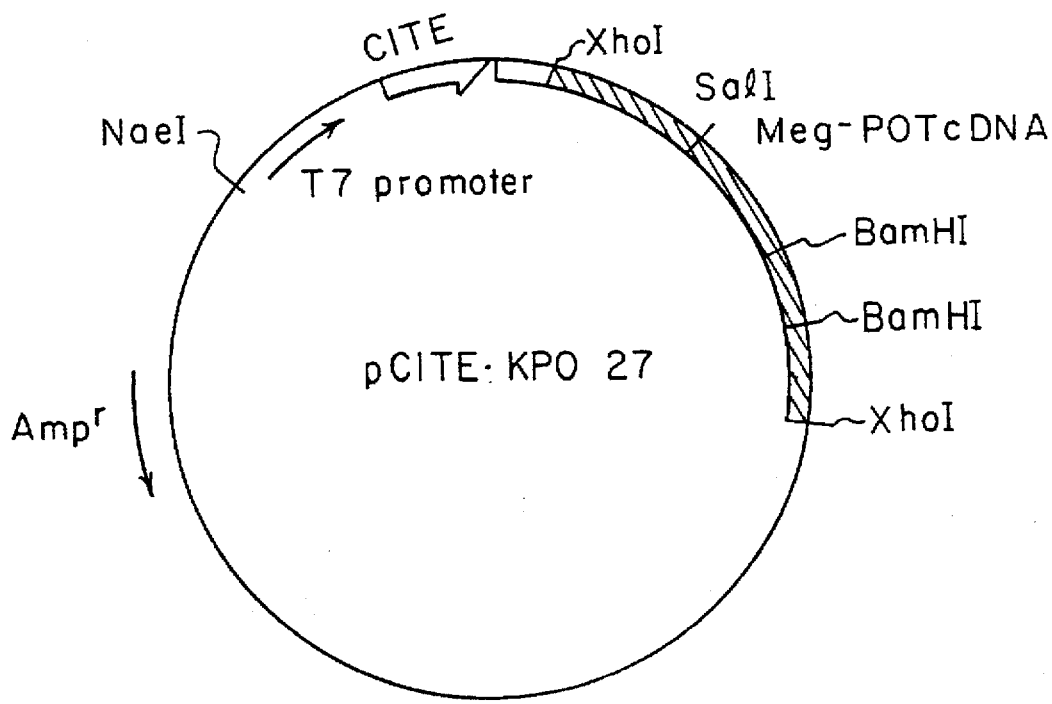
FIG. 5 shows the structure of plasmid pCITE KPO27.

The thus purified DNA was mixed with the previously obtained 1.9 kbp DNA fragment and the mixture incubated with T4 DNA ligase overnight at 16° C. in a 66 mM Tris-HCl buffer (pH 7.5) containing 6.6 mM $MgCl_2$, 5 mM DTT and 1 mM ATP. The ligation product was introduced into E. coli strain JM109 to clone pCITE.KPO27 (FIG. 5).

The plasmid pCITE.KPO27 was digested with restriction enzyme NaeI (Toyobo) at 37° C. for 2 h in a 10 mM Tris-HCl (pH 7.5) containing 10 mM $MgCl_2$ and 1 mM DTT and the digested DNA purified by treatment with phenol. Transcription of the digested DNA was performed by incubating the template DNA with T7 RNA polymerase at 37° C. in a 40 mM Tris-HCl buffer (pH 7.5) containing 2 mM spermidine, 6 mM $MgCl_2$, 10 mM NaCl, 1 U/µl of RNasin ribonuclease inhibitor (Promega), and 0.5 mM each of ATP, GTP, CTP and UTP. The resulting RNA was purified by treatment with phenol and recovered as a precipitate in ethanol. Subsequently, the RNA was translated into a $^{35}S$-methionine labelled reaction product using the Red Nova Lysate (Novagen). The reaction product was subjected SDS polyacrylamide gel electrophoresis and autoradiographed to demonstrate the presence of a band at a molecular weight of ca. 70,000.

EXAMPLE 20

Construction of Vector pMBPKPO27 (for E. coli)

Plasmid pKPO27 obtained in Example 8 was digested with restriction enzyme XhoI (Toyobo) at 37° C. for 2 h in a 20 mM Tris-HCl buffer (pH 8.5) containing 10 mM $MgCl_2$, 1 mM DTT and 100 mM KCl , and the digested DNA recovered as a precipitate in ethanol. The recovered DNA was further treated with the Klenow fragment of DNA polymerase at 10° C. for 1 h in a 20 mM Tris-HCl buffer (pH 7.4) containing 5 mM $MgCl_2$, 10 mM DTT, and 1 mM each of dATP, dCTP, dGTP and dTTP, and thereby blunt ends were created. The DNA was then subjected to agarose gel electrophoresis in order to recover a 1.9 kbp DNA fragment.

Vector pMAL-c (New England BioLabs) was digested with restriction enzyme StuI at 37° C. for 2 h in a 20 mM Tris-HCl buffer (pH 7.5) containing 10 mM $MgCl_2$, 1 mM DTT and 50 mM NaCl. Thereafter, alkaline phosphatase (Takara Shuzo) was added and the reactive solution was incubated at 65° C. for 2 h to effect dephosphorylation. The resulting DNA was deproteinated by treatment with phenol and recovered as a precipitate in ethanol.

Figure 6:
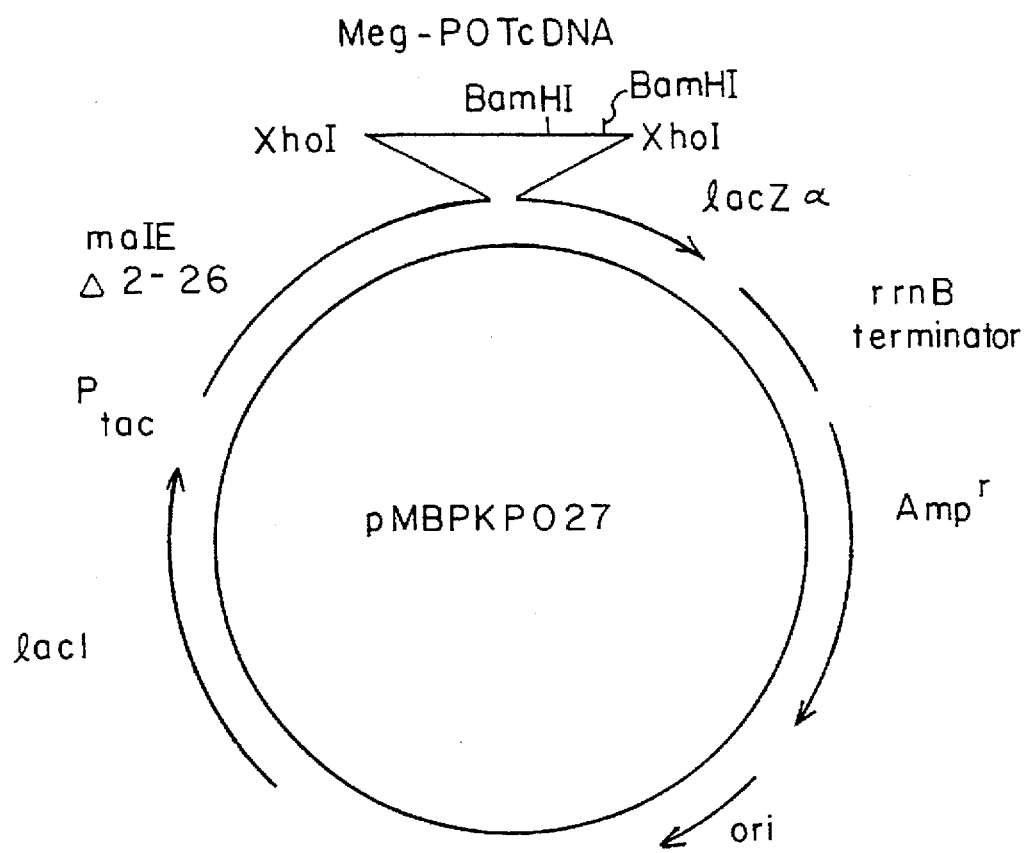
FIG. 6 shows the structure of plasmid pMBPKPO27.

The recovered DNA was mixed with the previously obtained 1.9 kbp DNA fragment and the mixture was incubated with T4 DNA ligase overnight at 16° C. in a 66 mM Tris-HCl buffer (pH 7.5) containing 6.6 mM $MgCl_2$, 5 mM DTT and 1 mM ATP. The ligation product was introduced into E. coli strain JM109 in order to clone pMBP-KPO27 (FIG. 6). As shown in FIG. 6, this plasmid encoded a fusion protein wherein the maltose binding protein (MBP) gene (malE Δ2–28) sequence, recognition sequence of Factor Xa, and the portion of Meg-POT cDNA extending downstream of and including amino acid 34, were inserted downstream of and in-frame with the tac promoter.

EXAMPLE 21

Expression of Fused Protein in E. coli Strain JM109

The host E. coli transformed with pMBPKPO27 in Example 20 was cultured at 37° C. for 16 h in 5 ml of an LB medium containing 50 µg/ml of ampicillin and 0.2% glucose. and the 4 ml of the liquid culture was added to 400 ml of LB medium containing 50 µg/ml of ampicillin and 0.2% glucose. Following culturing at 37° C. for about 2 h, isopropyl-β-D-thiogalactoside was added to a final concentration of 0.3 mM and incubation of the culture was continued for another 3 h. The cultured cells were subjected to SDS polyacrylamide electrophoresis and assayed by the Western blot technique with the anti-Meg-POT peptide serum or anti-MBP serum; the expression of a fused protein of MBP and Meg-POT was verified.

The expressed recombinant megakaryocyte potentiator (Meg-POT) was purified from the cultured cells in the following manner.

The sonicated cell suspension was sonicated for 20 min in 20 mM Tris-HCl buffer solution (pH 7.5), centrifuged in a SAC600 rotor, at 10,000 rpm for 30 min, at 4° C., in a Sorvall centrifuge, and the precipitated pellet suspended in distilled water. Thereafter, the suspension was centrifuged at 10,000% for 90 min, and the precipitated pellet dissolved in a 25 mM Tris-HCl buffer solution (pH 8.0) containing 1% 2-mercaptoethanol (2 ME) and 8M urea, and then centrifuged at 35,000 rpm for 60 min in order to remove the insoluble matter. The supernatant was diluted 2 fold with a 10 mM Tris-HCl buffer solution containing 10 mM 2 ME, 10 mM EDTA and 200 mM NaCl. The dilution was loaded on a 75 ml amylose column (BioLabs) equilibrated and washed with the same buffer solution. The proteins bound to the column were eluted with the same buffer solution containing 10 mM maltose. The eluted fractions were dialyzed against 20 mM Tris-HCl buffer solution (pH 7.4) that contained 2 mM $CaCl_2$ and 150 mM NaCl and which is a Factor Xa digestion buffer solution. Factor Xa was added to the dialyzed solution and the mixture was digested at 87° C. for 16 h. The reaction solution was concentrated using a PM-10 membrane filter (Amicon) and the concentrate passed through a PD-10 column equilibrated with the above-mentioned amylose column equilibrating buffer solution. The effluent was loaded on an amylose column and washed with the same buffer solution and the flow-through and washed fractions containing the recombinant megakaryocyte potentiator, were trained. These fractions were then concentrated on a Centriprep-10.

The thus yielded recombinant megakaryocyte potentiator was administered to rabbits together with Complete Freunds Adjuvant with 5 innoculations at 2-wk intervals. At day 10 following the final innoculation, blood was taken from rabbits through the carotid artery, thereby yielding an anti-Meg-POT anti-serum.

EXAMPLE 22

Construction of Vector pEFDKPOf (for Animal Cells)

Plasmid pKPO27 was digested with restriction enzyme EcoRI and BamHI (Takara Shuzo) at 37° C. in a 20 mM Tris-HCl buffer (pH 8.5) containing 10 mM $MgCl_2$, 1 mM DTT and 100 mM KCl. By subsequent agarose gel electrophoresis, a 1.8 kbp DNA fragment was recovered.

Vector DHFR-ΔE-RVh was likewise digested with EcoRI and BamHI and thereafter, treatment with alkaline phosphatase (Takara Shuzo) was conducted at 60° C. for 2 h to effect dephosphorylation. By subsequent agarose gel electrophoresis, a 7 kbp DNA fragment was recovered. This fragment was ligated with the previously obtained 1.8 kbp DNA fragment in order to construct pEFBKPO5'.

The plasmid pEFDKPO5' was digested with restriction enzyme BamHI at 37° C. in a 20 mM Tris-HCl buffer (pM 8.5) containing 10 mM $MgCl_2$, 1 mM DTT and 100 mM KCl. The recovered DNA was further treated with T4 DNA polymerase at 37° C. for 5 min in a 67 mM Tris-HCl buffer containing 6.7 mM $MgCl_2$, 16.6 mM $(NH_4)_2SO_4$, 10 mM 2 mercaptoethanol, 6.7 mM EDTA and 330 mM dNTP, and thereby blunt ends were created. Subsequent ligation with KpnI linkers (Amersham) yielded pEFDPO5'K.

Another batch of pKPO27 was digested with restriction enzyme XhoI at 37° C. in a 20 mM Tris-HCl buffer (pH 8.5) containing 10 mM $MgCl_2$, 1 mM DTT and 100 mM KCl. The recovered DNA was further treated with T4 DNA polymerase at 37° C. for 5 min in a 67 mM Tris-HCl buffer containing 6.7 mM $MgCl_2$, 16.6 mM $(NH_4)_2SO_4$, 10 mM 2 mercaptoethanol, 6.7 mM EDTA and 330 mM dNTP, and thereby blunt ends were created. The blunt-ended DNA was further treated with restriction enzyme SalI at 37° C. in a 50 mM Tris-HCl buffer (pH 7.5) containing 10 mM $MgCl_2$, 1 mM DTT and 100 mM NaCl. By subsequent agarose Eel electrophoresis, a 1.3 kbp DNA fragment was recovered.

Vector pCDM8 (Invitrogen) was digested with restriction enzyme XhoI at 37° C. in a 20 mM Tris-HCl buffer (pH 8.5) containing 10 mM $MgCl_2$, 1 mM DTT and 100 mM KCl. The recovered DNA was digested with restriction enzyme HpaI at 37° C. in a 20 mM Tris-HCl buffer (pH 8.5) containing 10 mM $MgCl_2$, 1 mM DTT and 100 mM KCl and thereafter, agarose gel electrophoresis was conducted to recover a 3.3 kbp DNA fragment. This fragment was ligated with the previously obtained 1.3 kbp DNA fragment to yield pCDMKPO3'.

Figure 7:
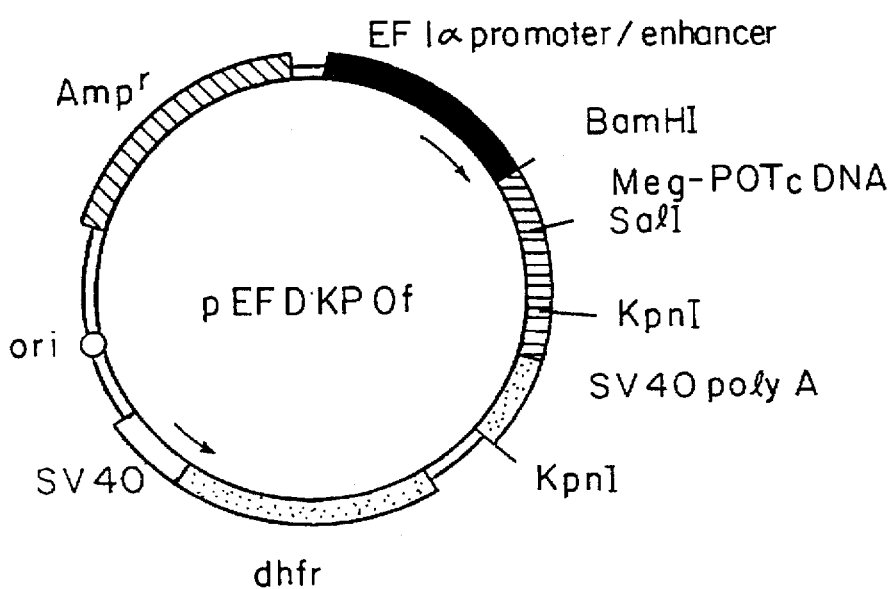
FIG. 7 shows the structure of plasmid pEFDKPOf.

Plasmids pEFDKPO5'K and pCDMKPO3' were digested with restriction enzyme KpnI at 37° C. in a 10 mM Tris-HCl buffer (pH 7.5) containing 10 mM $MgCl_2$ and 1 mM DTT. By subsequent agarose gel electrophoresis, two DNA fragments, one having a length of 10 kbp and the other 0.9 kbp, were recovered and ligated to yield pEFDKPOf (FIG. 7). As shown in FIG. 7, these plasmids contained a dihydrofolate reductase gene (dhfr) and had human Meg-POT cDNA inserted between the EF1α promoter and SV40 polyA signal.

Vector DHFR-ΔE-RVh was prepared by the following procedure using DHFR-ΔE-PMh-gγl and RVh-PMlf-4 which are described in International Publication WO92/19759. DHFR-ΔE-PMh-gγl and RVh-PMlf-4 were digested with restriction enzymes PvuI and BamHI (Takara Shuzo) at 37° C. in a 20 mM Tris-HCl buffer (pH 8.5) containing 10 mM $MgCl_2$, 1 mM DTT, 100 mM KCl and 0.01% BSA. By subsequent agarose gel electrophoresis, two DNA fragments were recovered, one having a length of 4 kbp and the other 3 kbp. These fragments were ligated to prepare DHFR-ΔE-RVh.

EXAMPLE 28

Expression of Megakaryocyte Potentiator (Meg-POT) in CHO Cells

CHO cells "DXB-11" were suspended in PBS to give a concentration of $1 \times 10^7$ cells/ml and 10 µg of pEFDKPOf was added to 0.8 ml of The resulting cell suspension. The plasmid was introduced into the CHO cells by electroporation with a GenePulsar (BioRad) at 1,900 V, 25 µF for 0.4 msec. Following a 10 min recovery period at room temperature, The electroporated cells were added to 25 ml of an α-MEM (Gibco) containing 10% fetal bovine serum. After growing for 24 h at 37° C., the cells were recovered by treatment with trypsin. 1% of the recovered cells were cultured for 3 wks in α-MEM medium (Gibco), a medium supplemented with 10% fetal calf serum (FCS) and which does not contain ribonucleoside or deoxyribonucleoside. During culturing, the medium was replaced once every 3 or 4 days. When colonies grew to a stage where they could be seen with the naked eye, clones were selected and subcultured individually. Thereafter, methotrexate (MTX, Sigma) was added to the α-MEM medium of the same composition and selective culturing was continued. The MTX concentration for the primary selection was 10 nM and the secondary selection was conducted for resistant clones in a medium having a MTX concentration of 50 nM. The selected clones were then subjected to large-scale cultivation in IMDM (Gibco) containing 50 nM MTX and 2% FCS, and the supernatant of the resulting culture purified.

Figure 8:
FIG. 8 shows the result of performing the Western blot technique using an antibody that was prepared against an antigenic synthetic peptide in the vicinity of the N terminus after analysis by SDS/PAGE of the supernatant of culture that was expressed in CHO cells (lane 1: molecular weight marker; lane 2: sample)

The purified supernatant of the culture was analyzed by SDS/PAGE and Meg-POT detection was conducted by the Western blot technique using an antibody against an antigenic synthetic peptide in the vicinity of the N terminus of Meg-POT. The prestained molecular weight markers were of the prestained type obtained from BioRad and used in Example 15. As FIG. 8 shows, three bands were detected at a molecular weight of ca. 33 kd, 30 kd and 27.5 kd.

EXAMPLE 24

Purification I of Recombinant megakaryocyte Potentiator (Meg-POT) from the Supernatant of the Culture of CHO Cells To 10 L of the supernatant of the culture of CHO cells purified in Example 23, Tween 20 was added to give a final concentration of 0.01% and then the supernatant was passed through a 5-µm membrane filter (Fuji Photo Film) to remove insoluble matter. A recombinant megakaryocyte potentiator (Meg-POT) was purified from the thus treated supernatant by the following procedure.

(i) The supernatant was loaded on a Blue-Sepharose fast flow column (5.0×20 cm, Pharmacia) equilibrated with a 50 mM Tris-HCl buffer (pH 8) containing 0.01% Tween 20 and 0.2M NaCl. After washing the column with the same buffer, the proteins adsorbed on the column were eluted with a 50 mM Tris-HCl buffer (pH 9) containing 0.01% Tween 20 and 2M KCl. The fractions were collected, concentrated with a Minitan filter (Millipore) and diluted through addition of a 20 mM acetate buffer (pH 5) containing 0.01% Tween 20; these procedures were repeated for desalting. The resulting insoluble matter was removed by centrifugation at 10,000 rpm for 30 min. The supernatant was subsequently purified by cation-exchange chromatography.

(ii) The fractions obtained in step (i) were loaded onto an S-Sepoarose fast flow column (5.0×12 cm) equilibrated with a 20 mM acetate buffer (pH 5) containing 0.01% Tween 20. After washing the column with the same buffer, the concentration of NaCl in that buffer was raised in order from 0.1 to 0.2, 0.3 and finally 0.5M so as to elute the proteins adsorbed on the column.

(iii) The 0.1M NaCl fraction containing the recombinant Meg-POT was loaded on a Vydac C4 column (10×280 mm) that had been equilibrated with 24% acetonitrile containing 0.1% TFA. The column was washed with the same eluting solution and thereafter, the concentration of acetonitrile in 0.1% TFA was raised linearly from 24 to 48% over 48 min, thereby eluting the proteins adsorbed on the column. The flow rate was 1.0 ml/min and protein detection was conducted at wavelengths 220 nm and 280 nm. The recombinant Meg-POT containing fractions having acetonitrile concentrations of 40–45% were collected and subjected to gel permeation chromatography as follows.

(iv) The recombinant Meg-POT containing fractions were loaded on a TSK gel G3000SW column (21.5×60 cm) equilibrated with acetonitrile containing 0.01% TFA. The flow rate was 3.0 ml/min and protein detection was conducted at 280 cm. The main peaks eluted at 37–44 min were collected, diluted with 0.1% TFA and subjected to reverse-phase HPLC under the same conditions as in (iii), thereby recovering the main peaks.

The recombinant megakaryocyte potentiator (Meg-POT) thus obtained was analyzed by SDS/PAGE on a 12% gel. The electrophoresis was conducted in accordance with the method of Laemmli (Nature, 227, 680, 1970) and the gel containing the electrophoresed samples was stained for protein with 2D-silver staining reagent "Dai-ichi" (Dai-ichi Kagaku Yakuhin). The molecular weight markers were of a low-molecular weight type obtained from BioRad [phosphorylase B (92.5 kd), bovine serum albumin (66.2 kd), ovalbumin (45.0 kd), carbonic anhydrase (31.0 kd), soybean trypsin inhibitor (21.5 kd), and lysozyme (14 kd)]. The resulting purified recombinant Meg-POT was detected as a single band at a molecular weight of ca. 33,000.

EXAMPLE 25

Amino Acid Sequence Analysis of the N- and C-Termini of the Recombinant Megakaryocyte Potentiator (Meg-POT)

(i) The recombinant Meg-POT of Example 24 was analyzed for N-terminal amino acid sequences by means of a gas-phase protein sequencer Model 476A (Applied Biosystems). As a result, three N-terminal amino acid sequences as listed below as (a), (b) and (c) were identified (SEQ. ID. NO.:18):

| | |
|---|---|
| Ser-Arg-Thr-Leu-Ala-Gly-Glu-Thr-Gly-Gln-Glu-Ala-Ala- | (a) |
| Leu-Ala-Gly-Glu-Thr-Gly-Gln-Glu-Ala-Ala-Pro-Leu-Asp- | (b) |
| Gly-Glu-Thr-Gly-Gln-Glu-Ala-Ala-Pro-Leu-Asp-Gly-Val- | (c) |

These sequences correspond to sequences (a), (b) and (c), respectively, which were identified in Example 13.

(ii) The C-terminal amino acid sequence of the recombinant Meg-POT was also sequenced. A solution of 70% formic acid (100 µl) containing 10 mg/ml of cyanogen bromide was added to the recombinant Meg-POT and cyanogen bromide cleavage was effected at room temperature for 24 h. Thereafter, excess reagents were removed by means of a centrifugal concentrator. The residue was dissolved in 0.1% TFA and loaded on a Vydac C4 column (4.6×250 mm) equilibrated with 0.1% TFA. The concentration of acetonitrile in 0.1% TFA was raised linearly up to 80% over 40 min, and thereby the cyanogen bromide fragments adsorbed on the column were eluted. Of the two resulting peaks, the C-terminal peptide fragment was further digested with Endo Asp-N as follows. The C-terminal peptide was dissolved in a 50 mM phosphate buffer (pH 8.0) and Endo Asp-N was added and thereby effecting enzymatic digestion at room temperature for 16 h. The pH of the reaction solution was adjusted to 3 by addition of 10% TFA and then the solution was loaded on a Vydac C18 column equilibrated with 0.1% TFA. Thereafter, the acetonitrile concentration was raised linearly from 0 to 48% over 48 min, thereby resulting in elution of the peptides adsorbed on the column. The resulting fragments were analyzed with a gas-phase protein sequencer Model 476A and the C-terminal fragment was found to have the following amino acid sequence (SEQ. ID. NO.:20):

Asp-Pro-Ser-Trp-Arg-Gln-Pro-Glu-Arg

EXAMPLE 28

Measuring the Activity of Megakaryocyte Potentiator (Meg-POT) in the Supernatant of the Culture of CHO Cells The megakaryocyte potentiator activity of the supernatant of the culture of CHO cells which was obtained in Example 23 and that of the recombinant Meg-POT purified in Example 24 were measured in accordance with the method already described hereinabove. From the results shown in Table 6 below, one can see that the supernatant of the culture of CHO cells into which a vector containing the cDNA of Meg-POT obviously exhibited the megakaryocyte potentiator activity. It is also clear that the Meg-POT purified from the same supernatant of culture also exhibited the megakaryocyte potentiator activity.

The protein content of the purified product was calculated for Ala=28 by the amino acid analysis technique.

TABLE 6

Activities of Megakaryocyte Potentiator in the Supernatant CHO Cell Cultures and Purified Recombinant Meg-POT

| | Sample's Final Concentration | Number of Megakaryocyte Colonies |
|---|---|---|
| Supernatant of | 0.08% | 4[a] |
| CHO Ceell | 0.31% | 11[a] |
| Cultures | 1.25% | 10.5[a] |
| | 5% | 12[a] |
| Purified | 0.01 ng/ml | 0[b] |
| Product | 0.1 ng/ml | 6[b] |
| | 1 ng/ml | 8[b] |
| | 10 ng/ml | 11[b] |

[a] The number of colonies formed minus the number of colonies (25) formed in the presence of IL-3 alone.
[b] The number of colonies formed minus the number of colonies (20.5) formed in the presence of IL-3 alone.

EXAMPLE 27

Purification II of Recombinant Megakaryocyte Potentiator (Meg-POT) from the Supernatant of the Culture of CHO Cells To 10 L of the supernatant of the culture of CHO cells as prepared in Example 23, Tween 20 was added to give a final concentration of 0.01% and the supernatant was passed through a 5 μm membrane filter (Fuji Photo Film) to remove insoluble matter. A recombinant megakaryocyte potentiator (Meg-POT) was purified from the thus treated supernatant by the following procedure.

(i) The supernatant was concentrated 20 times the initial concentration on a spiral cartridge (Amicon). To the stirred liquid concentrate at 4° C., Ammonium sulfate was added to give a final concentration which was 50% of the saturation value, the precipitated protein was centrifuged at 10,000 g for 30 min, collected as a precipitate, and then dissolved in a 10 mM Tris-HCl buffer solution (pH 7.4). Ammonium sulfate was added to the resulting fraction to give a concentration of 1M and the mixture was then subjected to hydrophobic chromatography as follows.

(ii) The fraction was added to a Phenyl-Sepharose 6FF column (5.0×15cm, Pharmacia) that had been equilibrated with a 10 mM Tris-HCl buffer solution (pH 7.4) containing 1M ammonium sulfate. After washing the column with the same buffer solution, the concentration of ammonium sulfate in that buffer was lowered to 0.1M and the column was washed again. Thereafter, the recombinant Meg-POT was eluted with a 10 mM Tris-HCl buffer solution (pH 8.5) containing 0.1% Tween 20. The eluted fractions were concentrated with a membrane filter PM-10 (Amicon), diluted 10 fold with a 10 mM Tris-HCl buffer solution (pH 8.5) containing 0.01% Tween 20, and then subjected to anion-exchange chromatography.

(iii) The fractions were loaded on a DEAE-Sepharose fast flow column (5×13 cm) equilibrated with a buffer solution of the same type used for dilution. After washing the column with the same buffer solution, the concentration of NaCl in the buffer solution was raised to 0.1M so as to elute the proteins adsorbed on the column. The fraction containing the recombinant Meg-POT was adjusted to a pH of 3 by addition of 10% TFA and subjected to reverse-phase HPLC under the following conditions.

(iv) The active fraction was loaded on a Vydac C4 column (10×250 mm) that had been equilibrated with 32% acetonitrile containing 0.1% TFA. The column was washed with the same eluting solution and thereafter, the concentration of acetonitrile in 0.1% TFA was raised linearly from 32 to 48% over 64 min, thereby eluting the proteins adsorbed on the column. The flow rate was 1.0 ml/min and protein detection was conducted at wavelengths 220 nm and 280 nm. The active fractions that were eluted at acetonitrile concentrations of 40–45% were collected and diluted 2 fold with 0.1% TFA. The dilution was subjected to reverse-phase HPLC under the same conditions as above and the main peaks eluting at acetonitrile concentrations of 40–45% were collected and subjected to gel permeation chromatography as follows.

(v) The active fractions were loaded on a TSK G3000SW column (21.5×60 cm) equilibrated with 40% acetonitrile containing 0.1% TFA. The flow rate was 3 ml/min and protein detection was conducted at 280 nm. The main peaks eluted at 42–47 min were collected and diluted with 0.1% TFA.

(vi) The active fractions were subjected to reverse-phase HPLC under the same conditions as in (iv), and thereby the main fractions were recovered.

When necessary, the recovered fractions were subjected to cation-exchange chromatography so as to remove the organic solvents and TFA. The thus treated fractions were diluted 10 fold with a 20 mM acetate buffer solution (pH 5.0) containing 0.01% Tween 20. The dilution was loaded on an S-Sepharose fast flow column equilibrated with the same buffer solution. After washing the column with the same buffer solution, the recombinant Meg-POT was eluted with a buffer solution of the same type as described above except that it contained 0.3M NaCl.

The recombinant megakaryocyte potentiator (Meg-POT) thus obtained was analyzed by SDS/PAGE on a 12% gel. The electrophoresis was conducted in accordance with the method of Laemmli (Nature, 227, 680, 1970) and the gel containing the electrophoresed samples was stained for protein with 2D-silver staining reagent "Dai-ichi" (Dai-ichi Kagaku Yakuhin). The molecular weight markers were of the low-molecular type obtained from BioRad and used in Example 15.

The purified recombinant Meg-POT was detected as a single band at a molecular weight of ca. 30,000.

The activity of this recombinant Meg-POT was measured by the same method as described above and compared with the data for the Meg-POT having a molecular weight of ca. 38,000 which was prepared in Example 26. As shown in Table 7, The Meg-POT having a molecular weight of ca. 30,000 did not have activity at any of the concentrations tested.

TABLE 7

Activity of Purified Megakaryocyte Potentiators

| Molecular weight Final concentration (ng/ml) | Meg-POT activity[a] | | | |
|---|---|---|---|---|
| | 40 | 10 | 2.5 | 0.625 |
| Ca. 33,000 | 11 | 8.5 | 5 | 7 |
| Ca. 30,000 | 1 | 0.5 | 0 | 1.5 |

[a] The number of colonies formed minus the number of colonies (25) formed in the presence of IL-3 alone.

EXAMPLE 28

Amino Acid Sequence Analysis II of the N- and C-Termini of the Recombinant Megakaryocyte Potentiator (Meg-POT)

(i) The recombinant Meg-POT having a molecular weight of ca. 30,000 which was prepared in Example 27 was analyzed for N-terminal amino acid sequences by means of a gas-phase protein sequencer Model 476A (Applied Biosystems). As a result, the three N-terminal amino acid sequences listed below as (a), (b) and (c) were identified (SEQ. ID. NO.:18):

Ser-Arg-Thr-Leu-Ala-Gly-Glu-Thr-Gly-Gln-Glu-Ala-Ala-  (a)

Leu-Ala-Gly-Glu-Thr-Gly-Gln-Glu-Ala-Ala-Pro-Leu-Asp-  (b)

Gly-Glu-Thr-Gly-Gln-Glu-Ala-Ala-Pro-Leu-Asp-Gly-Val-  (c)

These sequences correspond to sequences (a), (b) and (c), respectively, which were identified in Example 25.

(ii) The C-Terminal amino acid sequence of the recombinant Meg-POT was also analyzed. A solution of 70% formic acid (100 µl) containing 10 mg/ml of cyanogen bromide was added to the recombinant Meg-POT with a mol. wt. of ca. 30,000 and cyanogen bromide cleavage was effected at room temperature for 24 h. Thereafter, excess reagents were removed by means of a centrifugal concentrator, and the remainder of the sample dissolved in 0.1% TFA and loaded on a Vydac C4 column (4.6×250 mm) equilibrated with 0.1% TFA. The concentration of acetonitrile in 0.1% TFA was raised linearly up to 80% over 40 min, and thereby the cyanogen bromide fragments adsorbed on the column were eluted. The flow rate was 1 ml/min and peptide detection was conducted at 220 nm and 280 nm. The two peaks thus obtained were analyzed with a gas-phase protein sequencer Model 476A and the C-terminal fragment was found to have the following amino acid sequence (residues 1–16 of SEQ. ID. NO.:19):

Asp-Ala-Leu-Arg-Gly-Leu-Leu-Pro-Val-Leu-Gly-Gln-Pro-Ile-Ile-Arg

As one can see from the results of Examples 25–28, the amino acid sequences with molecular weights of ca. 33,000 and 30,000 were identical in terms of the N-terminal sequence and differed only with regard to the C-terminal sequence. The amino acid sequence having a molecular weight of ca. 33,000 exhibited the megakaryocyte potentiator activity but the one having a molecular weight of ca. 30,000 did not. One can therefore assume that an important site involved in the megakaryocyte potentiator activity may exist in the amino acid sequence of the C-terminus between the amino acid sequences having the molecular weight of ca. 33,000 and 30,000.

EXAMPLE 29

Purification III of Recombinant Megakaryocyte Potentiator (Meg-POT)

The Meg-POT fraction eluted with 2M KCl from the Blue-Sepharose fast flow column in Example 24 was treated by the following procedure.

Figure 9:
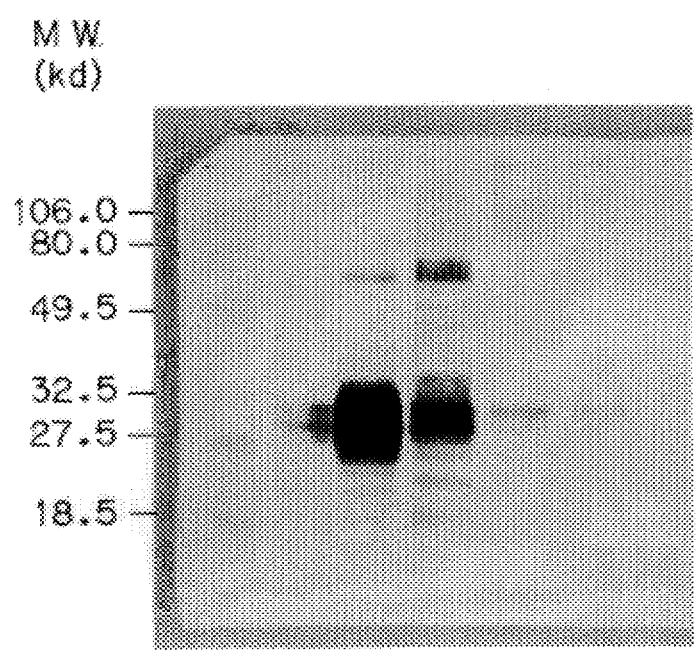
FIG. 9 shows the result of performing the Western blot technique using an antibody against the Meg-POT of Example 24 after analysis by SDS/PAGE of individual purified fractions of the supernatant of culture that was expressed in CHO cells (see Example 29 under (i)) (lane 1: molecular weight marker; lane 2: untrapped and washed fractions; lane 3: 0.1M NaCl fraction; lane 4: 0.2M NaCl fraction; lane 5: 0.3M NaCl fraction; lane 6: 0.5M NaCl fraction; lane 7: 1.0M NaCl fraction)

(i) The active fraction eluted with 2M KCl from the Blue-Sepharose fast flow column was desalted with a Minitan filter (Millipore) and ammonium sulfate was added to the desalted fraction at 4° C. to give a concentration which was 50% of the saturation level. The mixture was stirred for 30 min and the resulting precipitate was collected by centrifugation (10.000 g 30 min) and dissolved in distilled water. The solution was dialyzed overnight at 4° C. against a 10 mM Tris-HCl buffer solution (pH 8.0) containing 0.01% Tween 20 and the dialyzed solution loaded on a Q-Sepharose fast flow column (5×10 cm, Pharmacia) equilibrated with the same buffer solution. After washing the column with the same buffer solution, the concentration of NaCl in the same buffer solution was raised stepwise in order from 0.1 to 0.2, 0.3, 0.5 and finally 1.0M, and thereby the proteins adsorbed on the column were eluted. The individual fractions were subjected to SDS/PAGE and analyzed for Meg-POT by the Western blot technique using an antibody against the Meg-POT which was prepared in Example 23. The prestained molecular weight markers were obtained from BioRad [phosphorylase B (106 kd), bovine serum albumin (80.0 kd), ovalbumin (49.5 kd), carbonic anhydrase (32.5 kd), soybean trypsin inhibitor (27.5 kd) and lysozyme (18.5 kd)]. A stained band was detected at a molecular weight of ca. 70,000 (FIG. 9). In order to see whether this molecular species also had the Meg-POT activity, it was subjected to the following procedure of purification so that it could be separated from the molecular species having a molecular weight of ca. 33,000.

(ii) The 0.2M NaCl fraction containing the molecular species with a molecular weight of ca. 70,000 was adjusted to a pH of 5 by addition of acetic acid. Thereafter, the mixture was loaded on a Vydac C4 column equilibrated with 32% acetonitrile containing 0.1% TFA. After washing the column with the same eluting solution, the concentration of acetonitrile in 0.1% TFA was raised linearly from 32 to 48% over 40 min, and thereby the proteins adsorbed on the column were eluted. The fractions having acetonitrile concentrations of 39–41% were collected and subjected to gel filtration as follows.

Figure 10:
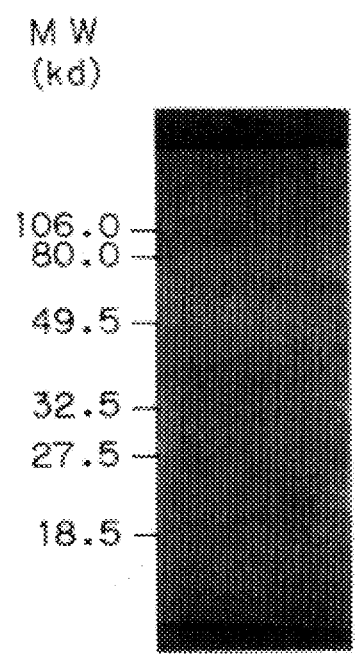
FIG. 10 shows the result of performance of the Western blot technique after analysis by SDS/PAGE of individual purified fractions of the supernatant of culture that was expressed in CHO cells (see Example 29 under (iii)) (lane 1: fraction eluted at 42–43 min; lane 2: fraction eluted at 43–44 min; lane 3: fraction eluted at 44–45 min; lane 4: fraction eluted at 45–46 min)

(iii) The collected fractions were diluted with PBS containing 0.01% Tween 20, concentrated with a Centriprep-10 filter and loaded on a TSK G3000SW column equilibrated with the same buffer solution. The flow rate was 3 ml/min and protein detection was conducted at wavelengths 220 nm and 280 nm. Fractionation was performed in 1 ml fractions and some fractions were measured for the Meg-POT activity by using the colony formation method. Following SDS/PAGE, the Meg-POT was detected by the Western blot technique. The molecular species having a molecular weight of ca. 70,000 was eluted from 42–46 min and no molecular species having a molecular weight of ca. 33,000 was detected in those fractions (FIG. 10). The molecular weight marker was of the above-described low-molecular weight type available from BioRad.

As in Example 26, the fractions eluting at 42–46 min were measured for their Meg-POT activity; the results are shown in Table 8. Since the Meg-POT activity was also observed in the fractions eluting at 42–46 min, it was thought that the molecular species with a molecular weight of ca. 70,000 also possessed the Meg-POT activity.

TABLE 8

Megakaryocyte Potentiator Activity of Fractions Purified from the Supernatant of CHO Cell Cultures

| Fractions from TSK G3000SW (min) | 42–43 | 43–44 | 44–45 | 45–46 |
|---|---|---|---|---|
| Megakaryocyte Potentiator Activity[a] | 12 | 8 | 10.5 | 5.5 |

[a]The number of colonies formed minus the number of colonies (19.5) formed in the presence of IL-3 alone.

EXAMPLE 30

Construction of Modified Meg-POT Expression Vectors and Their Expression in COS Cells (1) Construction of Vector pEFNKPOS
The-PCR was used to yield modified Meg-POT genes. As primers for PCR, the oligonucleotides identified below were synthesized with a 381A DNA Synthesizer (Applied Biosystems) on the basis of the gene's base sequence designated under SEQ ID No. 34:

Primer 3S (SEQ. ID. NO.:21): 5'-CTGGCTCACCG-GCTCTCTGA-3'

Primer G982A (SEQ. ID. NO.:22): 5'-ATGGATCCTTACCGCCG-GAACCGCGGCCG-3'BamHI

A Meg-POT gene was prepared wherein the gene coded for the sequence Arg-x-Arg-Arg$^{295}$(SEQ. ID. NO.:23); the recognition sequence of an animal endocellular processing enzyme Furin which is also located within the region of the C-terminus of Meg-POT purified from the supernatant of recombinant CHO cell cultures. An expression vector for this gene was constructed by using the same Meg-POT gene sequence.

Figure 11:
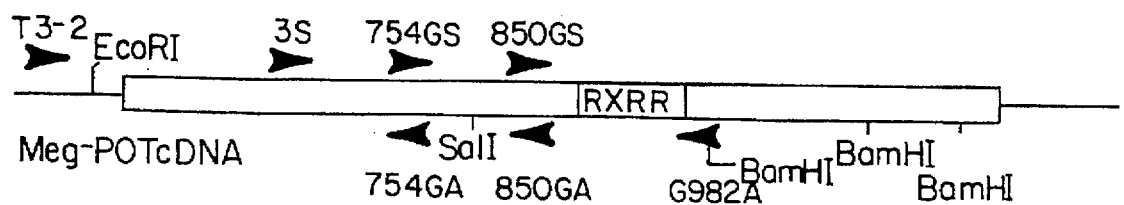
FIG. 11 shows the positions of the primers for PCR that was performed for constructing modified Meg-POT expression vectors.

With pKPO27 being used as a template, PCR was conducted with a DNA Thermal Cycler (Perkin Elmer Cetus). One microgram of pKPO27 was amplified in 100 µl of a PCR reactive solution containing 20 mM Tris-HCl (pH 8.8), 10 mM KCl, 6 mM $(NH_4)_2SO_4$, 2 mM $MgCl_2$, 0.1% Triton X-100, 0.1 mg/ml BSA, 100 mM deoxynucleotide triphosphate (dNTP) and 100 pmol each of the primers 3S and G982A. Following initial denaturation at 95° C. for 6 min, the DNA was cooled to 85° C. and 2.5 units of Pfu DNA polymerase (Stratagene) was added. Thereafter, the PCR was performed for 30 cycles, wherein each cycle consisted of a 1 min denaturation at 94° C., 30 sec annealing at 60° C., and 2 min elongation at 72° C. (FIG. 11). The sample was subjected to agarose gel electrophoresis and the amplified 590-bp DNA fragment was extracted. Using polynucleotide kinase, the 5' terminus of the DNA was phosphorylated and ligated to vector pSP73 which had been treated with restriction enzyme SmaI and alkaline phosphatase, and thereby pSP982A was constructed. The inserted base sequence was determined by the dideoxy sequencing procedure; G at the 982-position was found to have been replaced by T and there was a BamHI site at the 3' end of that sequence; it was verified that no other change had occurred.

Figure 12:
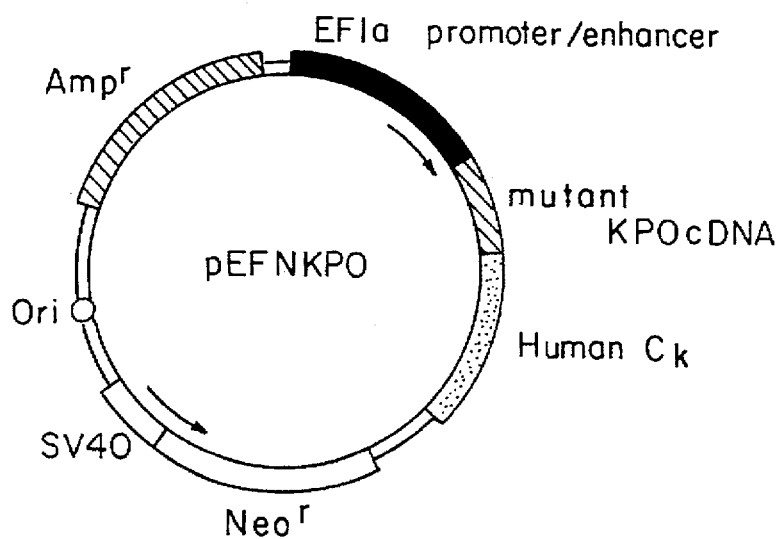
FIG. 12 shows the structures of modified Meg-POT expression vectors, pEFNKPOS, pEFNKPOL252V and pEFNKPOQ220E.

Following digestion with restriction enzymes SalI and BamHI, pSP982A and pRVHKPO27 were subjected to agarose gel electrophoresis so that a 190 bp and 9.5 kbp DNA fragment were recovered from the respective vectors and the two fragments ligated to produce pEFNKPOS (FIG. 12).

(2) Expression in COS Cells

COS cells were suspended in PBS to give a concentration of $1 \times 10^7$ cells/ml and 20 µg of pEFNKPOS was added to 0.8 ml of the resulting cell suspension. The respective plasmids were introduced into the COS cells by electroporation with a GenePulsar (BioRad) at 1,500 V and 25 µF. The electroporated cells were then added to DMEM (Gibco) containing 1% fetal bovine serum. After growing for 72 h, the supernatant of the cultures was collected, concentrated about 10 fold with a Centriprep-10 filter, and subjected to SDS polyacrylamide gel electrophoresis. In a separate step, rabbits were immunized with an antigenic Meg-POT protein that was expressed in *E. coli* and purified in Example 21. Using the thus prepared anti-Meg-POT antiserum, the Western blot technique was performed to verify the expression of a modified Meg-POT gene in the supernatant of the cultures.

The megakaryocyte potentiator activity of the supernatants was measured by the method already described herein. The results are shown in Table 9.

TABLE 9

Megakaryocyte Potentiator Activity in the Supernatant of COS Cell Cultures

| COS Cells % Concentration of the culture | Megakaryocyte Potentiator Activity[a] | | | | |
|---|---|---|---|---|---|
| supernatant | 10 | 5 | 2.5 | 1.25 | 0.625 |
| Control | 1 | 0 | 0 | 1 | 1 |
| pRVHKPO27f transformed | 9.5 | 9.5 | 6.5 | 12 | 0 |
| pEFNKPOS transformed | 9.5 | 0.5 | 1 | 0 | 0 |

[a]The number of colonies formed minus the number of colonies (40.5) formed in the presence of IL-3 alone.

(3) Construction of Amino Acid Substituted Meg-POT Expression Vector

As primers to be used in the PCR, the oligonucleotides identified below were synthesized with a 381A DNA Synthesizer (Applied Biosystems) on the basis of the gene's base sequence designated under SEQ ID No. 34:

Primer T3-2(SEQ. ID. NO.24): 5'-CATGATTACGCCAAGCTC-GAA-3'

Primer 754GA (SEQ. ID. NO.25): 5'-GCTGCCTCCTCCTGGTC-CTGGTCCAGGGGTCC-3'

Primer 754GS (SEQ. ID. NO.26): 5'-CCAGGACCAGGAGGAG-GCAGCCAGGGCGGC-3'

Primer 850GA (SEQ. ID. NO.27): 5'-AGCACGGGCACCAGGC-CCCGCAGAGCGTCC-3'

Primer 850GS (SEQ. ID. NO.28): 5'-CTGCGGGGCCTGGTGC-CCGTGCTGGGCCAGCCC-3'

A modified Meg-POT expression vector pEFNKPOL252V was constructed, in which Leu at the 252-position of pEFNKPOS was replaced by Val. Under the same conditions as described above, the PCR was performed on pKPO27 using two different primer combinations: T3-2+850GA and 850GS+G982A. The samples were subjected to gel electrophoresis and 0.9 kbp and 150 bp DNA fragment was extracted from the respective samples. These two DNA fragments were mixed and the subjected to another PCR using primers T3-2 and G982A (FIG. 11). Thereafter, agarose gel electrophoresis, an amplified 1 kbp DNA fragment was isolated. Using polynucleotide kinase, the 5' terminus of the DNA fragment was phosphorylated and ligated to vector pSP73 which was treated with restriction enzyme SmaI and alkaline phosphatase, and thereby pSP850G was yielded. The inserted base sequence was determined by the dideoxy sequencing procedure. The C at position 850 was found to have been replaced by G; the G at position 982 replaced by T; and the BamHI site located at the 3' end of the sequence: it was verified that no other changes had occurred. Following digestion with restriction enzymes SalI and BamHI, pSP850G and pRVHKPO27 were subjected to agarose gel electrophoresis so that a 190 bp and 9.5 kbp DNA fragment were recovered from the respective vectors and the two fragments ligated to produce pEFNKPOL252V (FIG. 12 ).

Also constructed was a modified Meg-POT expression vector pEFNKPOQ220E, in which Gln at the 220-position pEFNKPOS was replaced by Glu. Under the same conditions as described above, PCR was performed on pKPO27 using two different primer combinations; T3-2+754GA and 754GS+G982A. The samples were subjected to gel electrophoresis and a 0.9-kbp and 150-bp DNA fragment were extracted from the respective samples. The two DNA fragments were mixed and another PCR was conducted using the primers T3-2 and G982A. By agarose gel electrophoresis, an amplified 1 kbp DNA fragment was extracted. Using polynucleotide kinase, the 5' terminus of the DNA fragment was phosphorylated and ligated to vector pSP73 which had been treated with restriction enzyme SmaI and alkaline phosphatase, and thereby pSP754G was yielded. The inserted base sequence was determined by the dideoxy sequencing procedure. The C at position 754 was found to have been replaced by G; the G at position 982 replaced by T; and a BamHI site located at the 3' end of the sequence; it was verified that no other changes had occurred. Following digestion with restriction enzymes EcoRI and BamHI, pSP754G and pRVHKPO27 were subjected to agarose gel electrophoresis so that a 1 kbp and 8.7-kbp DNA fragment were recovered from the respective vectors and the two DNA fragments ligated to produce pEFNKPOQ220E (FIG. 12).

(4) Expression in Amino Acid Substituted Meg-POT in COS Cells

As described in (2) above, pEFNKPOL252V and pEFNKPOQ220E were introduced into COS cells by electroporation. The cells were cultured for 72 h and the supernatants of the two cultures concentrated about 10 fold with a Centriprep-10 filter, and the concentrated samples subjected to SDS polyacrylamide gel electrophoresis. In a separate step, rabbits were immunized with an antigenic Meg-POT protein that was expressed in *E. coli* and purified in Example 21. Using the thus prepared anti-Meg-POT antiserum, the Western blot technique was performed to verify the expression of a modified Meg-POT in the supernatants of culture.

---

We claim:

1. An isolated DNA molecule comprising a nucleotide sequence which encodes the amino acid sequence of SEQ ID NO:36.

2. A recombinant DNA vector comprising the DNA molecule of claim 1.

3. A host cell transformed or transfected with a vector according to claim 2.

4. A process for preparing a recombinant protein having megakaryocyte potentiator activity comprising:
   1) culturing a host cell according to claim 3 under conditions effective for expression of said DNA encoding the amino acid sequence of SEQ ID NO:36; and
   2) recovering a protein having the amino acid sequence of SEQ ID NO:36 so produced.

5. An isolated DNA molecule comprising a nucleotide sequence which encodes the amino acid sequence of SEQ ID NO:35.

6. A recombinant DNA vector comprising the DNA molecule of claim 5.

7. A host cell transformed or transfected with a vector according to claim 6.

8. A process for preparing a recombinant protein having megakaryocyte potentiator activity comprising:
   1) culturing a host cell according to claim 7 under conditions effective for expression of said DNA encoding the amino acid sequence of SEQ ID NO:35; and
   2) recovering a protein having the amino acid sequence of SEQ ID NO:35 so produced.

9. An isolated DNA molecule of claim 5, having the nucleotide sequence of SEQ ID NO:34.

10. A recombinant DNA vector comprising the DNA molecule of claim 9.

11. A host cell transformed or transfected with a vector according to claim 10.

12. A process for preparing a recombinant protein having megakaryocyte potentiator activity comprising:
   1) culturing a host cell according to claim 11 under conditions effective for expression of said DNA encoding the amino acid sequence of SEQ ID NO:35; and
   2) recovering a protein having the amino acid sequence of SEQ ID NO:35 so produced.

13. An isolated DNA molecule comprising a first DNA molecule which hybridizes to a second DNA molecule encoding the amino acid sequence of SEQ ID NO:35, under conditions equivalent to 50% formamide, 5× SSPE, 5× Denhardt's solution, 0.1% SDS and 0.1 mg/ml salmon sperm DNA at 42° C., or the complement thereof.

14. A recombinant DNA vector comprising the DNA molecule of claim 13.

15. A host cell transformed or transfected with a vector according to claim 14.

16. A process for preparing a recombinant protein having megakaryocyte potentiator activity comprising:

1) culturing a host cell according to claim 15, wherein said DNA molecule encodes the amino acid sequence of SEQ ID NO:35, under conditions effective for expression of said DNA encoding an amino acid sequence of SEQ ID NO:35; and 2) recovering a protein having the amino acid sequence of SEQ ID NO:35 so produced.

17. An isolated DNA molecule having the nucleotide sequence of SEQ ID NO:34, except that residue 1873 is an adenine residue.

18. A recombinant DNA vector comprising the DNA molecule of claim 17.

19. A host cell transformed or transfected with a vector according to claim 18.

20. A process for preparing a recombinant protein having megakaryocyte potentiator activity comprising:

1) culturing a host cell according to claim 19 under conditions effective for expression of said DNA encoding the amino acid sequence of SEQ ID NO:35, except that residue 593 is methionine; and 2) recovering a protein having the amino acid sequence of SEQ ID NO:35, except that residue 593 is methionine, so produced.

21. An isolated DNA molecule comprising a first DNA molecule which hybridizes to a second DNA molecule encoding the amino acid sequence of SEQ ID NO:36, under conditions equivalent to 50% formamide, 5× SSPE, 5× Denhardt's solution, 0.1% SDS and 0.1 mg/ml salmon sperm DNA at 42° C., or the complement thereof.

22. A recombinant DNA vector comprising the DNA molecule of claim 21.

23. A host cell transformed or transfected with a vector according to claim 22.

24. A process for preparing a recombinant protein having megakaryocyte potentiator activity comprising:

1) culturing a host cell according to claim 23, wherein said DNA molecule encodes the amino acid sequence of SEQ ID NO:36, under conditions effective for expression of said DNA encoding an amino acid sequence of SEQ ID NO:36; and 2) recovering a protein having the amino acid sequence of SEQ ID NO:36 so produced.

25. An isolated DNA molecule comprising a nucleotide sequence which encodes the amino acid sequence of SEQ ID NO:37.

26. A recombinant DNA vector comprising the DNA molecule of claim 25.

27. A host cell transformed or transfected with a vector according to claim 26.

28. A process for preparing a recombinant protein having megakaryocyte potentiator activity comprising:

1) culturing a host cell according to claim 27 under conditions effective for expression of said DNA encoding the amino acid sequence of SEQ ID NO: 37; and 2) recovering a protein having the amino acid sequence of SEQ ID NO:37 so produced.

29. An isolated DNA molecule comprising a first DNA molecule which hybridizes to a second DNA molecule encoding the amino acid sequence of SEQ ID NO:37, under conditions equivalent to 50% formamide, 5× SSPE, 5× Denhardt's solution, 0.1% SDS and 0.1 mg/ml salmon sperm DNA at 42° C., or the complement thereof.

30. A recombinant DNA vector comprising the DNA molecule of claim 29.

31. A host cell transformed or transfected with a vector according to claim 30.

32. A process for preparing a recombinant protein having megakaryocyte potentiator activity comprising:

1) culturing a host cell according to claim 31, wherein said DNA molecule encodes the amino acid sequence of SEQ ID NO:37, under conditions effective for expression of said DNA encoding an amino acid sequence of SEQ ID NO:37; and 2) recovering a protein having the amino acid sequence of SEQ ID NO:37 so produced.

* * * * *